US011903728B2

(12) United States Patent
Svanegaard et al.

(10) Patent No.: US 11,903,728 B2
(45) Date of Patent: Feb. 20, 2024

(54) METHODS OF CONFIGURING MEDICAL NOTIFICATIONS AND RELATED ACCESSORY DEVICES

(71) Applicant: Coloplast A/S, Humlebaek (DK)

(72) Inventors: Mads Hindhede Svanegaard, Bagsvaerd (DK); Esben Stroebech, Hoersholm (DK); Jacob Eisenberg, Greve (DK); Carsten Hellum Olsen, Frederiksberg (DK); Jeppe Malmberg, Copenhagen (DK); Alex Poulsen, Vaerloese (DK)

(73) Assignee: Coloplast A/S, Humlebaek (DK)

( * ) Notice: Subject to any disclaimer, the term of this patent is extended or adjusted under 35 U.S.C. 154(b) by 833 days.

(21) Appl. No.: 16/979,531

(22) PCT Filed: Mar. 15, 2019

(86) PCT No.: PCT/DK2019/050092
§ 371 (c)(1),
(2) Date: Sep. 10, 2020

(87) PCT Pub. No.: WO2019/174698
PCT Pub. Date: Sep. 19, 2019

(65) Prior Publication Data
US 2020/0405229 A1 Dec. 31, 2020

(30) Foreign Application Priority Data
Mar. 15, 2018 (DK) .......................... PA 2018 70166

(51) Int. Cl.
*A61F 5/443* (2006.01)
*A61F 5/44* (2006.01)
*A61B 5/00* (2006.01)

(52) U.S. Cl.
CPC .......... *A61B 5/4851* (2013.01); *A61B 5/6833* (2013.01); *A61B 5/742* (2013.01);
(Continued)

(58) Field of Classification Search
CPC ..... A61B 5/4851; A61B 5/6833; A61B 5/742; A61B 2562/0219; A61F 5/4404; A61F 5/443
See application file for complete search history.

(56) References Cited

U.S. PATENT DOCUMENTS 5,322,797 A * 6/1994 Mallow ................. G01N 31/22
436/3
5,816,252 A * 10/1998 Faries, Jr. ............. A61F 7/0241
128/849

(Continued)

Primary Examiner — Guy K Townsend
(74) Attorney, Agent, or Firm — Coloplast Corp., Coloplast A/S; Nick Baumann

(57) ABSTRACT

The present disclosure provides a method performed in an accessory device. The accessory device comprises an interface configured to communicate with one or more devices of an ostomy system. The interface comprises a display. The ostomy system comprises a monitor device, and/or an ostomy appliance configured to be placed on a skin surface of a user, wherein the ostomy appliance comprises the base plate. The method comprises displaying, on the display, a notification settings user interface comprising one or more control objects including a first control object, wherein the notification settings user interface is configured to adjust notification setting parameters of an ostomy user application. The method comprises while displaying the notification settings user interface, detecting, by contact, a first input directed to the first control object, in response to detecting the first input, in accordance with a determination that the first input meets one or more first control criteria: adjusting, based on the detected first input, a first notification setting parameter that corresponds to the first control object; and (Continued)

displaying an updated first control object in the notification settings user interface.

22 Claims, 23 Drawing Sheets

(52) U.S. Cl.
CPC ............ *A61F 5/443* (2013.01); *A61F 5/4404* (2013.01); *A61B 2562/0219* (2013.01)

(56) References Cited

U.S. PATENT DOCUMENTS

| | | | | |
|---|---|---|---|---|
| 6,101,867 A * | 8/2000 | Cavestri | ................ | G01M 3/20 252/301.16 |
| 6,171,289 B1 * | 1/2001 | Millot | ................ | A61F 5/443 604/336 |
| 7,014,816 B2 * | 3/2006 | Miller | ................ | G01N 33/02 422/86 |
| 8,061,360 B2 * | 11/2011 | Locke | ................ | A61M 1/73 128/898 |
| 8,343,437 B2 * | 1/2013 | Patel | ................ | G01D 3/10 436/2 |
| 8,398,603 B2 * | 3/2013 | Thirstrup | ................ | A61B 5/746 602/41 |
| 8,409,158 B2 * | 4/2013 | Edvardsen | ................ | A61F 5/443 604/335 |
| 8,500,718 B2 * | 8/2013 | Locke | ................ | A61H 9/0057 604/543 |
| 8,707,766 B2 * | 4/2014 | Harris | ................ | G01N 31/225 73/49.3 |
| 9,066,812 B2 * | 6/2015 | Edvardsen | ................ | A61F 5/443 |
| 9,216,104 B2 * | 12/2015 | Thirstrup | ................ | A61F 5/4404 |
| 10,016,298 B2 * | 7/2018 | Thirstrup | ................ | A61F 13/42 |
| 2004/0030305 A1 * | 2/2004 | Sakamoto | ................ | B29C 66/849 604/317 |
| 2006/0194324 A1 * | 8/2006 | Faries, Jr. | ................ | A61B 46/10 436/1 |
| 2008/0071214 A1 * | 3/2008 | Locke | ................ | F16M 13/02 604/151 |
| 2008/0234641 A1 * | 9/2008 | Locke | ................ | A61M 1/96 604/313 |
| 2009/0227969 A1 * | 9/2009 | Jaeb | ................ | A61M 1/74 604/313 |
| 2010/0030167 A1 * | 2/2010 | Thirstrup | ................ | A61F 5/4404 340/657 |
| 2011/0130642 A1 * | 6/2011 | Jaeb | ................ | A61M 1/90 600/407 |
| 2012/0143154 A1 * | 6/2012 | Edvardsen | ................ | A61F 5/4404 604/336 |
| 2012/0143155 A1 * | 6/2012 | Edvardsen | ................ | A61F 5/443 604/318 |
| 2013/0066285 A1 * | 3/2013 | Locke | ................ | A61F 13/0216 604/318 |
| 2013/0102979 A1 * | 4/2013 | Coulthard | ................ | A61M 1/784 604/319 |
| 2013/0231620 A1 * | 9/2013 | Thirstrup | ................ | A61F 5/445 604/344 |
| 2013/0324952 A1 | 12/2013 | Krystek et al. | | |
| 2015/0250639 A1 * | 9/2015 | Thirstrup | ................ | A61F 13/00051 156/278 |
| 2015/0257923 A1 * | 9/2015 | Thirstrup | ................ | A61F 13/42 604/318 |
| 2016/0158056 A1 * | 6/2016 | Davis | ................ | A61F 5/443 29/872 |
| 2017/0112658 A1 * | 4/2017 | Hosono | ................ | A61F 5/445 |
| 2017/0140103 A1 * | 5/2017 | Angelides | ................ | A61F 5/4404 |
| 2017/0340474 A1 * | 11/2017 | Thirstrup | ................ | A61B 5/746 |
| 2019/0133812 A1 * | 5/2019 | Seres | ................ | A61F 5/4404 |
| 2019/0192332 A1 * | 6/2019 | Hansen | ................ | A61B 5/7475 |
| 2020/0188161 A1 * | 6/2020 | Seres | ................ | G01K 13/00 |
| 2020/0375499 A1 * | 12/2020 | Hansen | ................ | A61B 5/4216 |
| 2020/0375784 A1 * | 12/2020 | Hansen | ................ | A61F 5/445 |
| 2020/0390587 A1 * | 12/2020 | Svanegaard | ................ | A61F 5/4404 |
| 2020/0395120 A1 * | 12/2020 | Svanegaard | ................ | A61B 5/4255 |
| 2020/0405228 A1 * | 12/2020 | Svanegaard | ................ | A61F 5/445 |
| 2020/0405229 A1 * | 12/2020 | Svanegaard | ................ | A61B 5/6833 |
| 2020/0405230 A1 * | 12/2020 | Svanegaard | ................ | A61B 5/6813 |
| 2021/0000414 A1 * | 1/2021 | Svanegaard | ................ | A61F 5/4404 |
| 2021/0000634 A1 * | 1/2021 | Svanegaard | ................ | A61B 5/0022 |
| 2021/0007663 A1 * | 1/2021 | Svanegaard | ................ | G16H 40/40 |
| 2021/0007881 A1 * | 1/2021 | Svanegaard | ................ | G01C 19/00 |
| 2021/0038424 A1 * | 2/2021 | Svanegaard | ................ | A61B 5/6843 |
| 2021/0059603 A1 * | 3/2021 | Svanegaard | ................ | A61F 5/443 |
| 2021/0369197 A1 * | 12/2021 | Hansen | ................ | A61B 5/7405 |
| 2022/0110585 A1 * | 4/2022 | Andersen | ................ | A61B 5/7264 |
| 2022/0241105 A1 * | 8/2022 | Hansen | ................ | A61B 5/441 |
| 2022/0304844 A1 * | 9/2022 | Carlsson | ................ | G01M 3/16 |
| 2023/0141719 A1 * | 5/2023 | Emborg | ................ | A61F 13/00051 710/105 |
| 2023/0142141 A1 * | 5/2023 | Emborg | ................ | A61B 5/742 604/318 |
| 2023/0146436 A1 * | 5/2023 | Hansen | ................ | A61B 5/4851 600/301 |
| 2023/0147665 A1 * | 5/2023 | Hasbeck | ................ | A61F 5/445 604/339 |
| 2023/0255811 A1 * | 8/2023 | Carlsson | ................ | G01M 3/16 604/332 |
| 2023/0284932 A1 * | 9/2023 | Hansen | ................ | A61B 5/68335 382/128 |
| 2023/0293333 A1 * | 9/2023 | Hansen | ................ | A61B 5/746 604/318 |

* cited by examiner

Tigger times of first electrode pair [h]

METHODS OF CONFIGURING MEDICAL NOTIFICATIONS AND RELATED ACCESSORY DEVICES

The present disclosure relates to an ostomy system and devices thereof. The ostomy system comprises an ostomy appliance, a monitor device and an accessory device. In particular, the present disclosure relates to a method of configuring ostomy notifications related to an ostomy appliance with a base plate, and related accessory devices.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
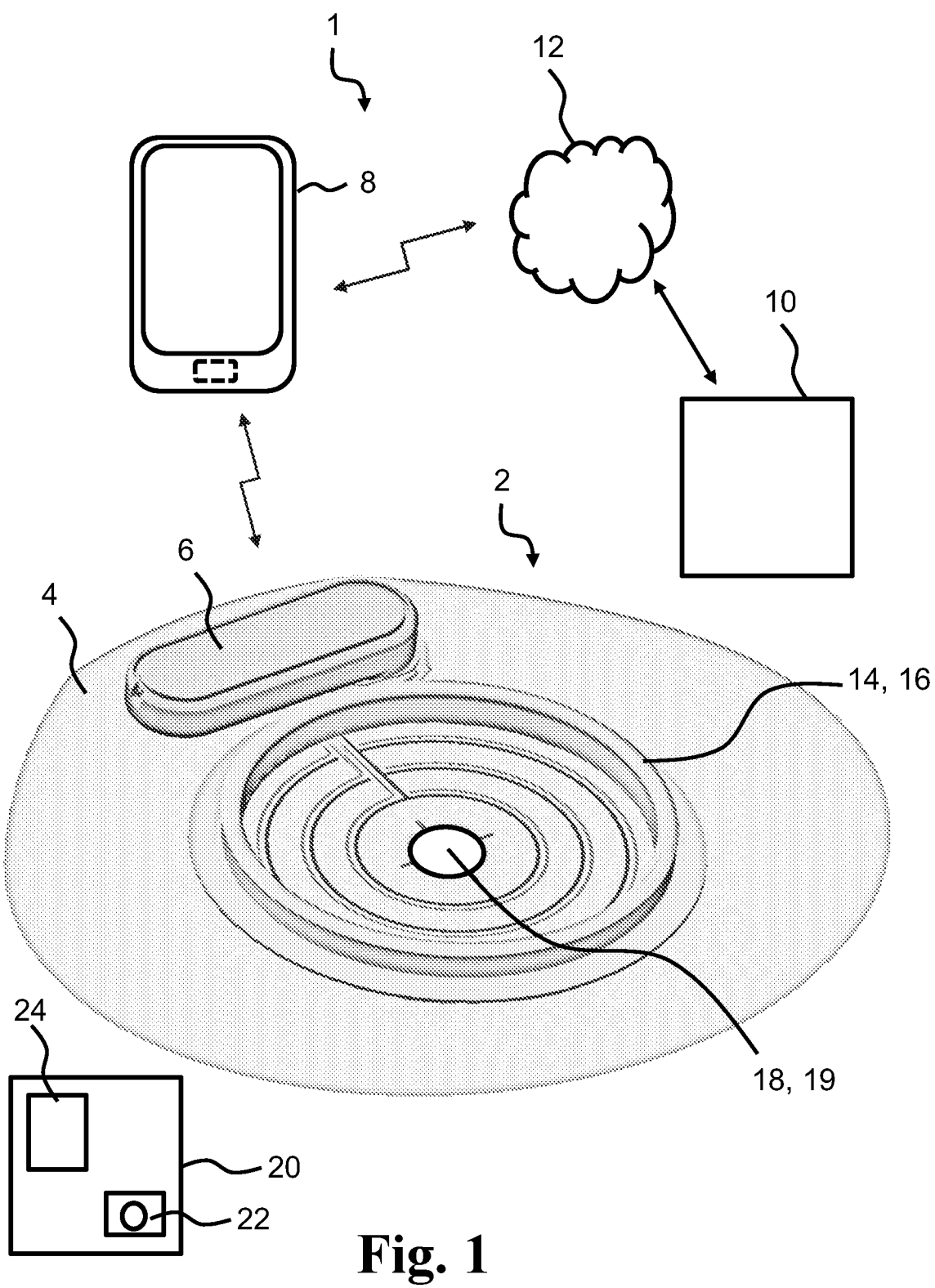
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance/monitor device. Likewise, whenever referring to the distal side or surface of a layer, an element, a device or part of a device, the referral is to the side or surface facing away from the skin, when a user wears the ostomy appliance/monitor device. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

A radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

An ostomy system comprising an ostomy appliance and a monitor device, the ostomy appliance comprising a base plate is disclosed, wherein the monitor device is a monitor device as described herein.

An ostomy system comprising a monitor device and an ostomy appliance comprising a base plate is disclosed, the base plate having a first adhesive layer with a proximal side configured for attachment of the base plate to the skin surface of a user, the first adhesive layer having a stomal opening with a center point, the monitor device comprising a processor and a sensor unit comprising a first sensor with a first sensor surface accommodated in a monitor device housing, the monitor device housing having a sensor opening in a proximal surface of the monitor device, the sensor opening forming at least a part of a sensor path from surroundings of the proximal surface to the first sensor surface.

Also disclosed is a monitor device for an ostomy appliance of an ostomy system, the monitor device comprising a processor and a sensor unit comprising a first sensor with a first sensor surface accommodated in a monitor device housing, the monitor device housing having a sensor opening in a proximal surface of the monitor device, the proximal surface configured for facing the skin of a user during use, the sensor opening forming at least a part of a sensor path from surroundings of the proximal surface to the first sensor surface.

The present disclosure provides an ostomy system and devices thereof, such as an ostomy appliance, a base plate for an ostomy appliance, a monitor device, and optionally one or more accessory devices which either alone or together may facilitate reliable monitoring of the ostomy appliance.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

A base plate for an ostomy appliance is disclosed, the base plate comprising a first adhesive layer with a proximal side configured for attachment of the base plate to the skin surface of a user, the first adhesive layer having a stomal opening with a center point; and a plurality of electrodes including a ground electrode, a first electrode, and a optionally a second electrode, the ground electrode comprising a ground connection part, the first electrode comprising a first connection part, and the second electrode comprising a second connection part, wherein the ground electrode forms a ground for the first electrode and/or the second electrode.

The base plate comprises a first adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate to the skin surface of a user. The first adhesive layer has a stomal opening with a center point or is at least prepared for forming a stomal opening with a center point. A base plate with three electrodes having sensing parts with contact to the first adhesive layer allows for determining erosion/swelling properties or characteristics of the first adhesive layer and/or determining a degree of erosion and/or swelling of the first adhesive layer.

It is an advantage of the present disclosure that an optimum or improved use of an ostomy appliance is provided. In particular, the present disclosure facilitates that a base plate is not changed too early (leading to increased cell-stripping from the skin and increased risk of skin damage and further leading to increased costs and/or material waste) nor too late (leading to adhesive failure, leakage and/or skin damage from the aggressive output). Accordingly, the user or a health care professional is able to monitor and plan the use of the ostomy appliance.

The present disclosure provides a simple, efficient, and easy-to-use ostomy appliance system with a high degree of comfort for a user.

The first adhesive layer may be made of a first composition. The first composition may comprise one or more polyisobutenes and/or styrene-isoprene-styrene. The first composition may comprise one or more hydrocolloids.

The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids, and synthetic hydrocolloids. The first composition may comprise 20-60% hydrocolloids. A preferred hydrocolloid is carboxymethyl cellulose (CMC). The first composition may optionally contain other components, such as fillers, tackifiers, plasticizers, and other additives.

The first adhesive layer may have a plurality of sensor point openings. A sensor point opening of the first adhesive layer is configured to overlap a (sensing) part of an electrode, e.g. to form a sensor point.

The sensor point openings of the first adhesive layer may comprise primary sensor point openings. The primary sensor point openings may comprise one or more primary first sensor point openings and one or more primary second sensor point openings, the primary first sensor point openings configured to overlap (sensing) parts of an electrode and the primary second sensor point openings configured to overlap (sensing) parts of another electrode different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap (sensing) parts of an electrode and the secondary second sensor point openings configured to overlap (sensing) parts of another electrode different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap (sensing) parts of an electrode and the tertiary second sensor point openings configured to overlap (sensing) parts of another electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm, such as 0.8 mm or 1.0 mm.

The first adhesive layer may have a primary thickness in a primary part of the first adhesive layer, e.g. in a primary region within a primary radial distance or in a primary radial distance range from the center point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the center point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate may comprise a second layer. The second layer may be an adhesive layer. The second layer may have a second radial extension that is larger than a first radial extension of the first adhesive layer at least in a first angular range of the base plate. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening with a center point.

The second adhesive layer may be made of a second composition. The second composition may comprise one or more polyisobutenes and/or styrene-isoprene-styrene. The second composition may comprise one or more hydrocolloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids, and synthetic hydrocolloids. The second composition may comprise 20-60% hydrocolloids. A preferred hydrocolloid is carboxymethyl cellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocolloids. For example, the second adhesive layer may provide a stronger attachment to the skin compared to attachment to the skin provided by the first adhesive layer. Alternatively, or additionally, the second adhesive layer may be thinner than the first adhesive layer. Alternatively, or additionally, the second adhesive layer may be less water and/or sweat absorbing than the first adhesive layer. Alternatively, or additionally, the second adhesive layer may be less moldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

The base plate comprises one or more electrodes, such as a plurality of electrodes, such as two, three, four, five, six, seven or more electrodes. The electrodes, e.g. some or all the electrodes, may be arranged between the first adhesive layer and the second adhesive layer. The electrodes may be arranged in an electrode assembly, e.g. an electrode layer. An electrode comprises a connection part for connecting the electrodes to other components and/or interface terminals/terminal elements. An electrode may comprise one or more conductor parts and/or one or more sensing parts. The electrode assembly may be arranged between the first adhesive layer and the second adhesive layer. The base plate, e.g. the electrode assembly, may comprise a first electrode, a second electrode and optionally a third electrode. The base plate, e.g. the electrode assembly, may comprise a fourth electrode and/or a fifth electrode. The base plate, e.g. the electrode assembly, optionally comprises a sixth electrode. The base plate, e.g. the electrode assembly, may comprise a ground electrode. The ground electrode may comprise a first electrode part. The first electrode part of the ground electrode may form a ground or reference for the first electrode. The ground electrode may comprise a second electrode part. The second electrode part of the ground electrode may form a ground or reference for the second electrode. The ground electrode may comprise a third electrode part. The third electrode part of the ground electrode may form a ground or reference for the third electrode. The ground electrode may comprise a fourth electrode part. The fourth electrode part of the ground electrode may form a ground or reference for the fourth electrode and/or the fifth electrode.

The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

The ground electrode may comprise a first electrode part and a second electrode part, the first electrode part forming the ground for the first electrode and the second electrode part forming the ground for the second electrode. The first electrode part may form a closed loop.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

Two electrodes of the electrode assembly may form a sensor. The first electrode and the ground electrode (e.g. first electrode part of the ground electrode) may form a first sensor or first electrode pair. The second electrode and the ground electrode (e.g. second electrode part of the ground electrode) may form a second sensor or second electrode pair. The third electrode and the ground electrode (e.g. third electrode part of the ground electrode) may form a third sensor or third electrode pair. The fourth electrode and the ground electrode (e.g. fourth electrode part of the ground electrode) may form a fourth sensor or fourth electrode pair. The fifth electrode and the ground electrode (e.g. fifth electrode part of the ground electrode) may form a fifth sensor or fifth electrode pair. The fourth electrode and the fifth electrode may form a sixth sensor or sixth electrode pair.

An electrode may comprise a sensing part or a plurality of sensing parts, i.e. the part(s) of an electrode that are used for sensing. The first electrode may comprise a first sensing part. The first sensing part may contact the first adhesive layer and is optionally arranged at least partly annularly around the stomal opening. The first electrode may comprise a first conductor part insulated from the first adhesive layer, e.g. by a masking element arranged between the first conductor part and the first adhesive layer. The first sensing part may extend at least 270 degrees around the stomal opening, such as at least 300 degrees around the stomal opening. The first sensing part of the first electrode may be arranged at a first ground distance from the first electrode part of the ground electrode. The first ground distance may be less than 5 mm, such as less than 3 mm, e.g. about 1.0 mm.

The second electrode may comprise a second sensing part. The second sensing part may contact the first adhesive layer. The second sensing part may be arranged at least partly annularly around the stomal opening. The second sensing part may extend at least 270 degrees around the stomal opening, such as at least 300 degrees around the stomal opening. The second sensing part of the second electrode may be arranged at a second ground distance from the second electrode part of the ground electrode. The second ground distance may be less than 5 mm, such as less than 3 mm, e.g. about 1.0 mm.

The first sensing part may be arranged at a first radial distance from the center point and the second sensing part may be arranged at a second radial distance from the center point. The second radial distance may be larger than the first radial distance. The second electrode may comprise a second conductor part insulated from the first adhesive layer, e.g. by a masking element arranged between the second conductor part and the first adhesive layer. The first radial distance may vary as a function of an angular position with respect to a zero direction from the center point. The second radial distance may vary as a function of an angular position with respect to a zero direction from the center point. The zero direction may be defined as the vertical upward direction when the base plate is in its intended wearing position on an upstanding user.

The first radial distance may be in the range from 5 mm to 40 mm, such as in the range from 10 mm to 25 mm, e.g. about 14 mm. The second radial distance may be in the range from 10 mm to 50 mm, such as in the range from 10 mm to 25 mm, e.g. about 18 mm.

The base plate may comprise a third electrode comprising a third connection part. The ground electrode may form a ground for the third electrode. The ground electrode may comprise a third electrode part, the third electrode part forming the ground for the third electrode. The third electrode may comprise a third conductor part insulated from the first adhesive layer, e.g. by a masking element arranged between the third conductor part and the first adhesive layer. The third electrode may comprise a third sensing part, the third sensing part contacting the first adhesive layer. The third sensing part may be arranged at least partly annularly around the stomal opening. The third sensing part may be arranged at a third radial distance from the center point. The third radial distance may be larger than the first radial distance and/or larger than the second radial distance. The third radial distance may be in the range from 15 mm to 50 mm. such as in the range from 20 mm to 30 mm, e.g. about 26 mm. The third sensing part may extend at least 270 degrees around the stomal opening, such as at least 300 degrees around the stomal opening. The third sensing part of the third electrode may be arranged at a third ground distance from the third electrode part of the ground electrode. The third ground distance may be less than 5 mm, such as less than 3 mm, e.g. about 1.0 mm. A base plate with a ground electrode, a first electrode, a second electrode, and a third electrode allows for a failsafe base plate in case e.g. the first electrode is cut or otherwise destroyed during preparation of the base plate.

The base plate may comprise a fourth electrode comprising a fourth connection part. The ground electrode may form a ground for the fourth electrode. The ground electrode may comprise a fourth electrode part, the fourth electrode part forming the ground for the fourth electrode. The fourth electrode may comprise one or a plurality of fourth sensing parts, such as at least five fourth sensing parts. The fourth sensing parts may be distributed around the stomal opening or a center point thereof. The fourth sensing parts may be arranged at respective fourth radial distances from the center point. The fourth radial distance(s) may be larger than the third radial distance. The fourth radial distance(s) may be in the range from 25 mm to 50 mm, such as about 30 mm The base plate may comprise a fifth electrode comprising a fifth connection part. The ground electrode may form a ground for the fifth electrode. The ground electrode may comprise a fifth electrode part, the fifth electrode part forming the ground for the fifth electrode. The fifth electrode may comprise one or a plurality of fifth sensing parts, such as at least five fifth sensing parts. The fifth sensing parts may be distributed around the stomal opening or a center point thereof. The fifth sensing parts may be arranged at respective fifth radial distances from the center point. The fifth radial distance may be larger than the third radial distance. The fifth radial distance may be equal to or larger than the fourth radial distance. The fifth radial distance(s) may be in the range from 25 mm to 50 mm, such as about 30 mm.

The first electrode may form an open loop. The second electrode may form an open loop and/or the third electrode may form an open loop. The fourth electrode may form an open loop. The fifth electrode may form an open loop. Open loop electrode(s) enables electrode arrangement in few or a single electrode layer.

The base plate may comprise a second adhesive layer, wherein the plurality of electrodes is arranged between the first adhesive layer and the second adhesive layer.

The electrode assembly may comprise a support layer, also denoted a support film. One or more electrodes may be formed, e.g. printed, on the proximal side of the support layer. One or more electrodes may be formed, e.g. printed, on the distal side of the support layer. Thus, one or more electrodes may be arranged between the support layer and the first adhesive layer. The electrode assembly may have a stomal opening with a center point.

The support layer may comprise polymeric (e.g. polyurethane, PTFE, PVDF) and/or ceramic (e.g. alumina, silica) materials. In one or more exemplary base plates, the support layer is made of thermoplastic polyurethane (TPU). The support layer material may be made of or comprise one or more of polyester, a thermoplastic elastomer (TPE), polyamide, polyimide, Ethylene-vinyl acetate (EVA), polyurea, and silicones.

Exemplary thermoplastic elastomers of the support layer are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The electrode assembly/base plate may comprise a masking element configured to insulate at least parts of the electrodes from the first adhesive layer of the base plate. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s). A sensor point opening of the masking element overlaps at least one electrode of the electrode assembly when seen in the axial direction, e.g. to form a sensor point. For example, a primary sensor point opening may overlap a (sensing) part of the ground electrode and/or a (sensing) part of the fourth electrode. A secondary sensor point opening may overlap a (sensing) part of the fourth electrode and/or a (sensing) part of the fifth electrode. A tertiary sensor point opening may overlap a (sensing) part of the fifth electrode and/or a (sensing) part of the ground electrode.

The masking element may comprise one or more, such as a plurality of, terminal openings. A terminal opening may overlap with one or more connection parts of electrodes. In one or more exemplary base plates, each terminal opening overlaps with a single connection part of an electrode.

The masking element may comprise polymeric (e.g. polyurethane, PTFE, PVDF) and/or ceramic (e.g. alumina, silica) materials. In one or more exemplary base plates, the masking element is made of or comprises thermoplastic polyurethane (TPU). In one or more exemplary base plates, the masking element is made of or comprises polyester. The masking element material may be made of or comprise one or more of polyester, a thermoplastic elastomer (TPE), polyimide, polyimide, Ethylene-vinyl acetate (EVA), polyurea, and silicones.

Exemplary thermoplastic elastomers of the masking element are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate may comprise a first intermediate element. The first intermediate element may be arranged between the electrodes/electrode layer and the first adhesive layer and/or between the second layer and the first adhesive layer. The first intermediate layer may be made of an insulating material.

The base plate may comprise a release liner. The release liner is a protective layer that protects adhesive layer(s) during transport and storage and is peeled off by the user prior to applying the base plate on the skin. The release liner may have a stomal opening with a center point.

The base plate may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening with a center point. The top layer may have a thickness in the range from 0.01 mm to 1.0 mm, e.g. in the range from 0.02 mm to 0.2 mm, such as 0.04 mm. The top layer may have a stomal opening with a center point.

The base plate comprises a monitor interface. The monitor interface may be configured for electrically and/or mechanically connecting the ostomy appliance (base plate) to the monitor device. The monitor interface may be configured for wirelessly connecting the ostomy appliance (base plate) to the monitor device. Thus, the monitor interface of the base plate is configured to electrically and/or mechanically couple the ostomy appliance and the monitor device.

The monitor interface of the base plate may comprise, e.g. as part of a first connector of the monitor interface, a coupling part for forming a mechanical connection, such as a releasable coupling between the monitor device and the base plate. The coupling part may be configured to engage with a coupling part of the monitor device for releasably coupling the monitor device to the base plate.

The monitor interface of the base plate may comprise, e.g. as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes (connection parts) of the base plate/electrode assembly. The first intermediate element may be arranged between the terminal elements and the first adhesive layer. The first intermediate element may cover or overlap terminal element(s) of the base plate when seen in the axial direction. Thus, the first adhesive layer may be protected or experience more evenly distributed mechanical stress from the terminal elements of the base plate, in turn reducing the risk of terminal elements penetrating or otherwise damaging the first adhesive layer. The first intermediate element may protect or mechanically and/or electrically shield the first adhesive layer from the terminal elements of the base plate.

A terminal element, such as the ground terminal element, the first terminal element, the second terminal element, the third terminal element, the fourth terminal element, the fifth terminal element and/or the sixth terminal element, may comprise a distal end and a proximal end. A terminal element, such as the ground terminal element, the first terminal element, the second terminal element, the third terminal element, the fourth terminal element, the fifth terminal element and/or the sixth terminal element, may comprise a distal part, a centre part, and/or a proximal part. The distal part may be between the distal end and the centre part. The proximal part may be between the proximal end and the centre part. The proximal end/proximal part of a terminal element may contact a connection part of an electrode. A terminal element, such as the ground terminal element, the first terminal element, the second terminal element, the third terminal element, the fourth terminal element, the fifth terminal element and/or the sixth terminal element, may be gold plated copper.

The base plate may comprise a coupling ring or other coupling member for coupling an ostomy pouch to the base plate (two-part ostomy appliance). The center point may be defined as a center of the coupling ring.

The base plate has a stomal opening with a center point. The size and/or shape of the stomal opening is typically adjusted by the user or nurse before application of the ostomy appliance to accommodate the user's stoma. In one or more exemplary base plates, the user forms the stomal opening during preparation of the base plate for application.

The monitor device comprises a processor. The processor controls the operation of the monitor device including collection and processing of ostomy data from the base plate of the ostomy appliance, processing of, such as storing, sensor data from sensor unit, and generation/transmission of monitor data to accessory devices.

The monitor device comprises a memory for storing ostomy data and/or parameter data based on the ostomy data. The processor may be configured for processing and storing sensor data in the memory.

The monitor device comprises a monitor device housing optionally made of a plastic material. The monitor device housing may be an elongate housing having a first end and a second end. The monitor device housing may have a length or maximum extension along a longitudinal axis in the range from 1 cm to 10 cm. The monitor device housing may have a width or maximum extension perpendicular to the longitudinal axis in the range from 0.5 cm to 5 cm, such as from 0.8 cm to 3 cm. The monitor device housing may be curve-shaped.

The monitor device housing may have a plurality of sensor openings, e.g. a plurality of sensor openings for a sensor and/or a sensor opening for each of a plurality of sensors. The monitor device may comprise one or more sensor openings in a distal surface of the monitor device. The monitor device may comprise one or more sensor openings in a side surface of the monitor device. The monitor device may comprise one or more sensor openings in an end surface of the monitor device.

The sensor opening in the proximal surface is arranged at a sensor opening distance from the first end. The sensor opening distance, also denoted $D\_S$, may be in the range from 0.25 L to 0.75 L, such as from 0.35 L to 0.65 L, where L is the length of the monitor device housing. The sensor opening distance may be in the range from 10 mm to 70 mm.

The monitor device housing comprises or forms a sensor path from surroundings of the proximal surface to the first sensor surface. The sensor path translates temperature and/or humidity at the proximal surface of the monitor device/monitor device housing to the first sensor surface. The sensor opening forms a part of the sensor path and has a cross-sectional area optionally in the range from 0.2 mm$^2$ to 10 mm$^2$. The sensor opening may be a circular opening with a diameter in the range from 0.3 mm to 1.4 mm, e.g. from 0.6 mm to 1.0 mm.

The monitor device comprises a sensor unit with one or more sensors including a first sensor. The sensor unit is connected to the processor for feeding sensor data to the processor. The sensor unit may comprise a humidity sensor for provision of humidity data to the processor. Thus, the sensor data may comprise humidity data. For example, the first sensor may be a humidity sensor for provision of humidity data to the processor. Thus, the present disclosure enables humidity detection near the skin of a user and/or on the distal side of the base plate, which in turn can be used for a more accurate estimation of base plate operation state.

The sensor unit may comprise a temperature sensor for provision of temperature data to the processor. Thus, the sensor data may comprise temperature data. For example, the first sensor may be a temperature sensor for provision of temperature data to the processor. Thus, the present disclosure enables temperature detection near the skin of a user and/or on the distal side of the base plate, which in turn can be used for a more accurate estimation of base plate operation state.

The first sensor may be a combined humidity and temperature sensor for provision of humidity and temperature data to the processor.

The sensor unit of the monitor device may comprise a second sensor, e.g. an accelerometer for provision of acceleration data to the processor. The sensor unit of the monitor device may comprise a third sensor, e.g. a gyroscope for provision of gyroscope data to the processor. The sensor unit of the monitor device may comprise a fourth sensor, e.g. a magnetometer for provision of magnetometer data to the processor.

The processor is configured for processing ostomy data obtained from the base plate and generate or determine monitor data that are transmitted to an accessory device. The monitor data may comprise sensor data obtained from the sensor unit.

The monitor device comprises a first interface for connecting the monitor device to the base plate. The first interface may be arranged in the proximal surface of the monitor device housing. The first interface may be arranged within a first interface distance from the first end. The first interface distance may be less than 0.50 L, such as less than 0.4 L, where L is the length of the monitor device housing.

The monitor device may comprise a sealing element forming a seal between the first sensor and a housing part of the monitor device housing. The sealing element may be an O-ring, e.g. made of a rubber material. The sealing element may encircle the first sensor surface to expose the first sensor surface (membrane) to the sensor path while providing a closed cavity of the monitor device, the closed cavity accommodating PCB, processor, and other electronic circuitry. A glue may form the sealing element.

The ostomy system enables a reliable and accurate measurement of different parameters relevant for monitoring of the ostomy appliance. In the ostomy system, a distance between the proximal surface of the monitor device and a distal surface of the base plate, in a coupled state, is in the range from 0.2 mm to 10 mm, such as in the range from 0.5 mm to 5 mm. In the coupled state, the monitor device is attached to the base plate and arranged in its intended position during use of the ostomy system.

The monitor device comprises a first interface connected to the processor. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and/or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part for forming a mechanical connection, such as a releasable coupling between the monitor device and the base plate. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively. The processor may be configured to transmit monitor data, as a wireless monitor signal via the antenna and the wireless transceiver.

The ostomy system may comprise a docking station forming an accessory device of the ostomy system. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

The present disclosure provides a method performed in an accessory device. The accessory device comprises an interface configured to communicate with one or more devices of an ostomy system. The interface comprises a display. The ostomy system comprises a monitor device, and/or an ostomy appliance configured to be placed on a skin surface of a user, wherein the ostomy appliance comprises the base plate. The method comprises displaying, on the display, a notification settings user interface comprising one or more control objects including a first control object, wherein the notification settings user interface is configured to adjust notification setting parameters of an ostomy user application. The method comprises while displaying the notification settings user interface, detecting, by contact, a first input directed to the first control object, in response to detecting the first input, in accordance with a determination that the first input meets one or more first control criteria: adjusting, based on the detected first input, a first notification setting parameter that corresponds to the first control object; and displaying an updated first control object in the notification settings user interface.

The method may be seen as method for controlling ostomy notification settings, e.g. configuring ostomy notifications related to an operating state of a base plate disclosed herein.

The method comprises displaying, on the display, a notification settings user interface comprising one or more control objects including a first control object (e.g. one or more control user interface objects including a first control user interface object). A notification settings user interface may refer to a user interface for controlling (e.g. configuring) ostomy notification settings of an ostomy user application that controls an ostomy appliance disclosed herein, such as settings of ostomy notifications. The notification settings user interface may be referred to as ostomy notification settings user interface. Notification settings may form part of a settings of an ostomy user application, e.g. general settings of an ostomy user application. The notification settings user interface is configured to adjust notification setting parameters of an ostomy user application, including a first notification setting parameter, a second notification setting parameter, a third notification setting parameter, and/or a fourth notification setting parameter. The notification setting parameters may comprise a frequency of notification, a time to notify, a recurrence, and/or a time to change ostomy appliance. A time to notify is a time period where a notification is to be generated and displayed. The notification setting parameters may comprise an indicator of the user experience in using an ostomy appliance.

An ostomy user application is a user application related to the ostomy appliance, which enables a monitoring of the base plate of the ostomy appliance by the user, and a management of information and actions related to the ostomy appliance and ostomy care. An ostomy user application is configured to run on a processor of the accessory device and to store application data in a memory of the accessory device. A user interface refers herein to a graphical representation comprising a collection of user interface objects. A user interface comprises one or more user interface objects. A user interface may be referred to as a user interface screen.

A user interface object refers herein to a graphical representation of an object that is displayed on the display of the accessory device. The user interface object may be user-interactive, or selectable by a user input. For example, an image (e.g., icon), a button, and text (e.g., hyperlink) each optionally constitute a user interface object. The user interface object may form part of a widget. A widget may be seen as a mini-application that may be used by the user, and created by the user. A user interface object may comprise a prompt, application launch icon, and/or an action menu.

A control object refers to a user interface object configured to control settings of notifications related to an ostomy appliance, such as settings of ostomy notifications.

The notification settings user interface is configured to adjust notification setting parameters of an ostomy user application, e.g. the ostomy user application installed on the accessory device. For example, the notification settings user interface allows the user adjusting notification setting parameters of an ostomy user application. The notification settings user interface comprises one or more control objects, wherein any of one of the one or more control objects are configured to allow the user adjusting notification setting parameters of an ostomy user application.

The method comprises while displaying the notification settings user interface, detecting, e.g. by contact, a first input directed to the first control object. For example, detecting, by contact, a first input directed to the first control object may comprise detecting a touch input directed to the first control object. For example, detecting a first input directed to the first control object may comprise detecting an input using an input device (e.g. a keyboard) in an input field of the first control object. The input device can be a keyboard, an interactive screen, a pointing device, and the like for inputting data.

The method may comprise: in response to detecting the first input, determining whether the first input meets one or more first control criteria and in accordance with a determination that the first input meets one or more first control criteria: adjusting, based on the detected first input, a first notification setting parameter that corresponds to the first control object.

The method comprises: in response to detecting the first input, in accordance with a determination that the first input meets one or more first control criteria: adjusting, based on the detected first input, a first notification setting parameter that corresponds to the first control object. For example, adjusting, based on the detected first input, a first notification setting parameter that corresponds to the first control object comprises controlling (e.g. toggling, gradually changing) the first notification setting parameter according to the detected first input.

The notification settings user interface may comprise a first control object for controlling a first notification setting parameter, a second control object for controlling a second notification setting parameter, a third control object for controlling a third notification setting parameter, a fourth control object for controlling a fourth notification setting parameter.

The method comprises displaying an updated first control object in the notification settings user interface e.g. according to the adjusting.

The first input may comprise a touch (e.g. a tap, a force touch, a long press), and/or a movement of contact (e.g. a swipe gesture, e.g. for toggling). The movement on contact may be detected by a touch sensitive surface, e.g. by a touch sensitive display. The first input may comprise a lift off. The first input may comprise a touch, and a movement followed by a lift off.

The display of the accessory device may be configured to detect touch (e.g. the display is a touch-sensitive display), the input comprises a contact on the touch sensitive display. A touch-sensitive display provides an input interface and an output interface between the accessory device and a user. A processor of the accessory device may be configured to receive and/or send electrical signals from/to touch-sensitive display. A touch-sensitive display is configured to display visual output to the user. The visual output optionally includes graphics, text, icons, video, and any combination thereof (collectively termed "graphics"). For example, some or all of the visual output may be seen as corresponding to user-interface objects.

The present disclosure provides an efficient, and readily accessible user interface for adjusting notification settings of an ostomy user application used for monitoring performance of a base plate of an ostomy appliance. The present disclosure provides an improved degree of comfort for a user by providing timely notifications regarding the operating state of the base plate of the ostomy appliance, which is not accessible or visible by the user or the health care professional.

The disclosed methods and accessory devices allow to customize the notifications communicating the dynamic internal of the ostomy appliance to a user, which supports the user in coordinating the use of the ostomy appliance with the planning of daily life activities. The disclosed methods and accessory devices provide notification settings of ostomy notifications allows adjusting notifications to user needs, such as privacy needs, comfort needs, security needs, and/or hygiene needs.

It is an advantage of the present disclosure that a user of an ostomy appliance or a health care professional is able to obtain one or more ostomy notifications to plan changes of the base plate of the ostomy appliance in his/her daily life. The disclosed methods and accessory devices may reduce a potential risk of future leakage by providing timely a notification. Thus, the present disclosure may help reducing the risk of a user experiencing leakage (e.g. faecal material leakage coming out from the ostomy appliance) from an ostomy appliance while being subtly notified of any needed change or operating state of the base plate.

A reduction of the risk of leakage in turn helps in reducing risks of skin damage to a user (as it supports the prevention of leakage due to e.g. adhesive erosion, malfunctions and misplacement of the ostomy appliance on the stoma).

Further, it is seen that the present disclosure provides a clear distinction or differentiation between the following events in the present and the future: adhesive failure, leakage (incl. partial leakage) of faecal material which is harmful to the skin, and a sweating ostomate.

The one or more first control criteria may comprise a primary criterion that is met when a characteristic feature of the first input exceeds a threshold during the first input. The one or more first control criteria may comprise a primary criterion that is met when a characteristic feature of the contact exceeds a threshold during the first input. The characteristic feature of the contact may comprise intensity of contact exceeding a first intensity threshold (deep press) or being below the first intensity threshold (light press), magnitude of movement of the first input (distance travelled on the screen, speed), and/or a duration of input. For example, the primary criterion is met when a characteristic feature of the first input exceeds a distance threshold, an intensity threshold, a speed threshold, a duration threshold. For example, when the first input involves a movement exceeding a distance threshold (e.g. of zero mm), the primary criterion is met. For example, when the first input involves an intensity exceeding an intensity threshold (e.g. of deep press threshold), the primary criterion is met. For example, when the first input involves a movement exceeding a speed threshold, the primary criterion is met. For example, when the first input involves a duration exceeding a duration threshold (e.g. of 3s), the primary criterion is met.

In one or more exemplary methods and accessory devices, the one or more first control criteria are met when the primary criterion is met.

Adjusting, based on the detected first input, a first notification setting parameter may comprise adjusting, based on the characteristic feature of the detected first input, a first notification setting parameter. For example, adjusting, based on the detected first input, a first notification setting parameter may comprise adjusting the first notification setting parameter based on the movement of the detected first input. For example, adjusting, based on the detected first input, a first notification setting parameter may comprise adjusting the first notification setting parameter based on the intensity of the detected first input (e.g. an increased intensity of the first input may result in an increased frequency of notification). For example, adjusting, based on the detected first input, a first notification setting parameter may comprise adjusting the first notification setting parameter based on the duration of the detected first input (e.g. an increased duration of first input may result in an increased frequency of notification).

The method may comprise generating, based on the adjusted notification setting, one or more notifications including a first notification. The first notification is displayed as a user interface object notifying the user of the operating state of the base plate. The first notification may be displayed as part of a widget, such as a widget displayed in a widget user interface screen.

Generating, based on the adjusted notification setting, the one or more notifications may comprise obtaining monitor data from the one or more devices, and obtaining context data. Obtaining monitor data from the one or more devices may comprise obtaining the monitor data from the monitor device coupled with the ostomy appliance, such as from the ostomy appliance (e.g. from the base plate), such as from a server device in a network. The method may comprise obtaining monitor data from a memory of the accessory device. Obtaining monitor data from the monitor device may comprise retrieving and/or receiving the monitor data from the monitor device.

In one or more exemplary methods, context data comprises application data, e.g. from a second application. Context data may refer to data indicative of a context in which the ostomy appliance may be operating, such as data characterizing the context or an environment affecting the operation of the ostomy appliance and of the base plate. For example, context data may be referred to as contextual data.

The ostomy appliance comprises a base plate, such as a base plate disclosed herein. The ostomy appliance comprises an ostomy pouch. The base plate may comprise a first adhesive layer having a proximal side. During use, a proximal surface of the first adhesive layer adheres to the user's skin in the peristomal area and/or to additional seals, such as sealing paste, sealing tape and/or sealing ring. The base plate may comprise one or more electrodes configured to measure electrical properties of the first adhesive layer. The electrical properties may be indicative of a conductive path in the first adhesive layer, thereby indicative of the moisture level, and indicative of the condition of the ostomy appliance.

The monitor data may be indicative of a condition of the ostomy appliance, e.g. a condition of the base plate disclosed herein. The condition of the ostomy appliance or of the base plate disclosed herein may refer to a level of a physical property of at least a part of the ostomy appliance, such as a level of moisture and/or temperature of at least a part of the base plate, such as a level of a physical property of at least a layer of the base plate, such as a level of moisture and/or temperature of at least a layer of the base plate, such as a level of a physical property of at least an adhesive layer of the base plate (e.g. a first adhesive layer proximal to the skin of the user). In one or more exemplary accessory devices, the interface is configured to obtain the monitor data by obtaining the monitor data indicative of the condition comprising a moisture level of a first adhesive layer of the base plate and/or a moisture level of a proximal side of the first adhesive layer. The moisture level may be seen as representative of a conductive path in the first adhesive layer, such as across the first adhesive layer. The monitor data comprises e.g. data representative of the measurement of the electrical properties of the first adhesive layer. In other words, the condition may be seen as a condition of the first adhesive layer.

The monitor data may comprise ostomy data and/or parameter data. The monitor device is configured to process the ostomy data and/or parameter data based on the ostomy data to determine monitor data that is transmitted to the accessory device. The ostomy data and/or parameter data may be indicative of resistance between electrodes of the base plate, capacitance and/or inductance between electrodes and/or any change thereof. For example, the ostomy data and/or parameter data may be indicative of a change in resistance, capacitance and/or inductance between electrodes. For example, the ostomy data and/or parameter data may comprise timing information, such as timestamped data or information from which timing is derivable.

Generating, based on the adjusted notification setting, the one or more notifications may comprise determining one or more operating states of the ostomy appliance based on the monitor data and the context data.

An operating state is indicative of future adhesive performance of the base plate of the ostomy appliance. Generating, based on the adjusted notification setting, the one or more notifications may comprise generating the one or more notifications based on the adjusted first notification setting parameter and the one or more operating states.

An operating state may comprise at least one of: a wear time, a quality of adhesion, and a moisture pattern representation. Wear time may comprise average wear time, nominal wear time, minimal wear time, maximal wear time, median wear time, and/or any of other statistical metric derivable from wear time. Wear time may comprise remaining wear time and/or current wear time and/or elapsed wear time. A quality of adhesion may comprise a metric indicative of erosion of a layer of the base plate (such as of the first adhesive layer), such as a moisture pattern representation.

An operating state in the present disclosure is indicative of the dynamic internal state of the base plate of the ostomy appliance (e.g. of the base plate currently being worn by the user) related to adhesive performance of the base plate. Adhesive performance of the ostomy appliance may be related to an internal condition of the ostomy appliance (e.g. of the base plate of the ostomy appliance), such as an internal condition of an adhesive layer of the base plate. The adhesive performance, and thereby the operating state may be affected by several factors, such as humidity, temperature, misplacement of the ostomy appliance on the stoma, and/or malfunction of the ostomy appliance. The adhesive performance, and thereby the operating state may be related to misplacement of the of the base plate on the stoma, and/or malfunction of the of the base plate. The one or more factors alone or in combination impact the adhesive performance of the of the base plate. The operating state may be varying in time. The operating state can be indicative of a degree of erosion of the base plate (e.g. radial erosion, and/or transverse erosion), e.g. a degree of erosion of a layer of the base plate, e.g. a degree of erosion of the first adhesive layer. The operating state can be indicative of presence of fluid on a proximal surface of the first adhesive layer.

Many of the factors may be captured by context data obtained at the accessory device. Thus, exploiting context data and correlating it with monitor data is seen as leading to an improvement in determining future operating states (e.g. improved accuracy and timeliness of the determined future operating states), and thereby an improvement in the life of an ostomist (because the ostomist given a more accurate future operating state is able to plan and prevent any undesired situation caused by e.g. the ostomy appliance leaking).

Adhesive performance may be indicative of wear property, e.g. wear time and/or wear comfort.

In one or more exemplary accessory devices, an operating state is configured to indicate whether the base plate is properly operational based on its adhesive performance (e.g. wear property, e.g. wear time and/or wear comfort).

For example, the operating state may be indicative of the severity and/or imminence of a leakage (e.g. low, medium, acute). The operating state may comprise Z operating states, where Z is an integer. The operating state may comprise a first operating state, a second operating state, and/or a third operating state (e.g. good, check, change in X time/NOW).

Generating the one or more notifications based on the adjusted first notification setting parameter and the one or more operating states may comprise determining whether at least one of the one or more operating states meets one or more notification criteria (e.g. being in an operating state indicative of imminent leakage, or acute leakage). Generating the one or more notifications based on the adjusted first notification setting parameter and the one or more operating states may comprise in accordance with the determination that at least one of the one or more operating states meets one or more notification criteria: generating the one or more notifications including the first notification based on the adjusted notification setting; and displaying the one or more notifications including the first notification on the display.

The one or more operating states may comprise at least one of: a wear time, a quality of adhesion, and a moisture pattern representation.

Obtaining the context data may comprise obtaining the context data from a second application different from the ostomy user application. For example, the second application comprises a calendar application, a weather application, a health application, a sports application, an activity tracker application, an analysis application, a photo application, a camera, and/or a medical application.

Context data may be quantified with one or more context parameters, which may be associated one or more adjustment coefficients. The accessory may maintain a local or remote database (or lookup table) associating a context parameter with a corresponding adjustment coefficient. Determining the future operating state of the base plate of the ostomy appliance based on the monitor data and the context data may comprise determining the future operating state of the base plate of the ostomy appliance based on the monitor data and the one or more context parameters (e.g. using the one or more adjustment coefficients).

In an illustrative example where the present technique is applied, initially, the operating state of the base plate may be indicative of a default or normal operating state of the base plate wherein the default operating state is indicative of very low or no degree of radial erosion of the base plate and/or of no leakage. After a prolonged use of the ostomy appliance, the accessory device may determine an operating state of the ostomy appliance that may be indicative of a degree of radial erosion of the base plate, such as of the first adhesive layer, and/or an acute leakage risk of the ostomy appliance.

Obtaining the context data may comprise obtaining the context data comprising calendar data from a calendar application installed on the accessory device. Calendar data comprises date, time, calendar events including event date, event start time, event end time, event recurrence, event location, event attendees, etc.

Generating, based on the adjusted first notification setting parameter, one or more notifications may comprise generating the one or more notifications based on the adjusted first notification setting parameter and the calendar data. The method may comprise deriving one or more regular events not derived from the calendar application, such as commuting, going up and down stairs, walking dog etc. For example, the accessory device can determine one or more operating states based on a calendar event being a sports activity. The accessory device may have adjusted the notification parameter related to sport activity to e.g. notify the user of the operating state of the base plate at least 1 h before the sport activity starts. If the operating state of the base plate indicates a medium risk of leakage before the sports activity, the accessory device may determine the future operating as being of higher risk of leakage at any time during the sports activity due to e.g. sweating and movements affecting the adhesive performance of the base plate. The accessory may display the notification 1 h before the sport activity is scheduled to start according to the corresponding notification parameters. This way, the user is informed and may change the base plate prior to the sports activity.

Obtaining the context data may comprise obtaining the context data comprising location data, e.g. derived from location sensor data, derived from connectivity data. Location data may be obtained from a GPS sensor, an accelerometer, a cellular base station, a wireless access point, and/or a short range connection.

Generating, based on the adjusted first notification setting parameter, one or more notifications may comprise generating the one or more notifications based on the adjusted first notification setting parameter and location data. The notification thereby derived may be based on location of the accessory device with respect to locations of one or more changing rooms. For example, the notification settings indicated that the notification is to be displayed when the location data indicates that a changing room is in the vicinity and when the accessory device has determined that the operating state is of at least medium risk of leakage.

Displaying the one or more notifications including the first notification may comprise displaying the one or more notifications including the first notification on a locked screen. Displaying the one or more notifications including the first notification may comprise displaying the one or more notifications including the first notification on an unlocked screen.

In one or more exemplary methods, when the accessory device is in a locked state, the method comprises detecting an authentication input to unlock the device; in response to detecting the authentication input to unlock the device, verifying the authentication input; unlocking the accessory device in accordance with successful verification of the authentication input; and in response to unlocking of the accessory device, in accordance with successful verification of the authentication input, displaying a first user interface including the first notification (e.g. overlaid on the first user interface). The authentication input may comprise a biometric input (e.g. face recognition, iris scanning and recognition, gaze detection, fingerprint detection), passcode.

In one or more exemplary methods, the method comprises detecting a biometric input, in response to detecting the biometric input, verifying the biometric input; in accordance with successful verification of the biometric input, displaying the one or more notifications including the first notification comprises displaying a long version of the first notification; in accordance with unsuccessful verification of the biometric input, displaying the one or more notifications including the first notification comprises displaying a short version of the first notification. Displaying the one or more notifications including the first notification comprises for example displaying, on the display, the first notification indicative of one or more operating states (e.g. on the lock screen and/or on the home screen of the accessory device).

In one or more exemplary methods, the method comprises detecting a second input selecting the first notification; in response to detecting the second input, opening the ostomy user application. When the display is a touch sensitive display, the second user input may comprise a contact on the touch sensitive display.

In one or more exemplary methods, the method comprises in response to opening the ostomy user application, displaying a second user interface comprising a third user interface object representing the current operating state of the ostomy appliance and a fourth user interface object representing the one or more future operating states of the ostomy appliance.

The present disclosure provides an accessory device. The accessory device forms part of an ostomy system. The accessory device comprises a memory; a processor operatively connected to the interface and to the memory; and an interface configured to communicate with one or more devices of the ostomy system. The one or more devices comprising a monitor device, and/or an ostomy appliance configured to be placed on a skin surface of a user; wherein the ostomy appliance comprises a base plate. The interface comprises a display and optionally a transceiver, and optionally an input device (e.g. a keyboard, a microphone). The accessory device is configured to perform any of the method disclosed herein.

The interface comprises a display, such as a touch-sensitive display. The interface of the accessory device is configured to communicate with one or more of: a user, a monitor device and/or a server device. The interface of the accessory device may be configured to communicate with the server device via a network.

The interface may comprise a monitor interface for connecting, e.g. wirelessly connecting, the accessory device to one or more monitor devices. The interface of the accessory device may comprise a transceiver comprising an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5.

The accessory device is configured to receive monitor data from one or more monitor devices. The accessory device may be configured to transmit accessory data, e.g. to a server device. For example, the processor of the accessory device may be configured to transmit accessory data, as a wireless accessory signal via the antenna and the wireless transceiver.

The interface of the accessory device comprises a display.

The interface may be configured to obtain, via the transceiver, monitor data from the monitor device coupled to the ostomy appliance. The monitor data may comprise sensor data obtained from one or more sensors in the monitor device. The monitor data may comprise ostomy data obtained from electrodes of the base plate, and/or parameter data based on ostomy data obtained from electrodes of the base plate.

The present disclosure provides an ostomy appliance system comprising an ostomy appliance disclosed herein, an accessory device disclosed herein, and a monitor device disclosed herein, the ostomy appliance comprising a base plate disclosed herein.

The present disclosure provides a computer readable storage medium storing one or more programs, the one or more programs comprising instructions, which when executed by an accessory device with an interface, a memory and a processor cause the accessory device to perform any of the methods disclosed herein. FIG. 1 illustrates an exemplary ostomy system. The ostomy system 1 comprises an ostomy appliance 2 including a base plate 4 and an ostomy pouch (not shown). Further, the ostomy system 1 comprises a monitor device 6 and an accessory device 8 (mobile telephone). The base plate 4 and the monitor device 6 are in a coupled state, and the monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data to determine monitor data that are transmitted to the accessory device 8. The monitor data may include sensor data of the monitor device. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate 4 has a stomal opening 18 with a center point 19. The size and/or shape of the stomal opening 18 is typically adjusted by the user or nurse before application of the ostomy appliance to accommodate the user's stoma. The ostomy system 1 optionally comprises a docking station 20 forming an accessory device of the ostomy system 1. The docking station comprises 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

Figure 2:
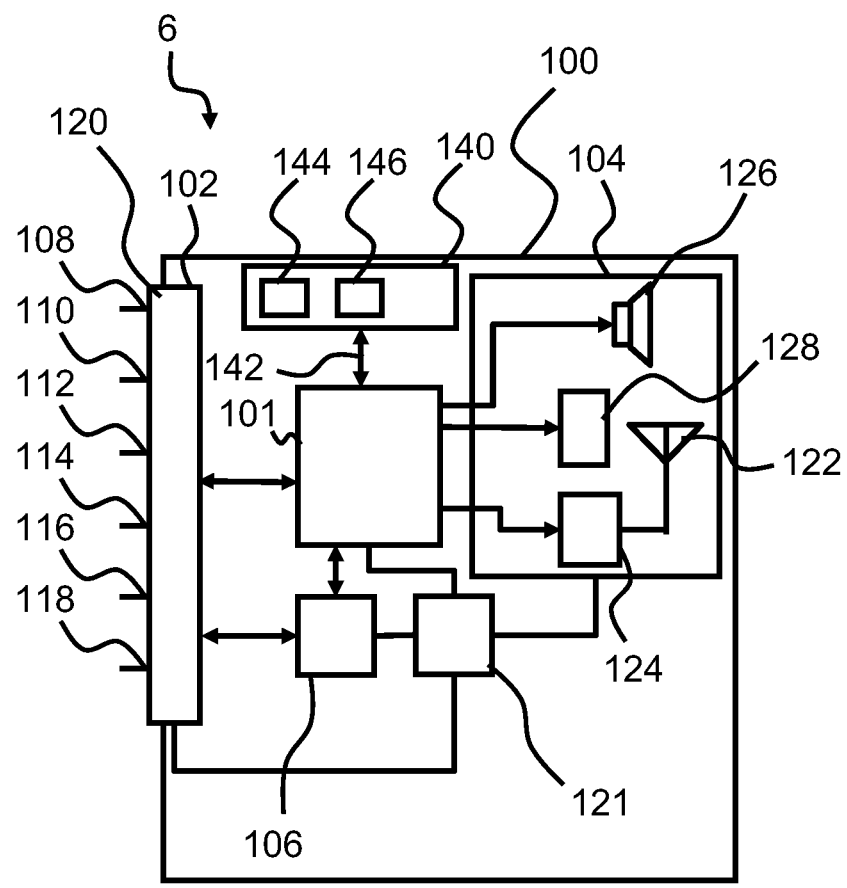
FIG. 2 illustrates an exemplary monitor device of the ostomy system.

FIG. 2 is a schematic block diagram of an exemplary monitor device. The monitor device 6 comprises a monitor device housing 100, a processor 101, and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 comprises a sensor unit 140 connected to the processor 101 for provision of sensor data 142 to the processor 101. The sensor unit 140 comprises a first sensor 144 being a temperature and humidity sensor for feeding temperature and humidity data as sensor data 142 to the processor 101. Further, the sensor unit 140 comprises a second sensor 146 being an accelerometer for feeding acceleration data as sensor data 142 to the processor 101. The processor 101 receives and stores sensor data 142 comprising temperature data, humidity data, and acceleration data, in the memory 106 and/or transmits the sensor data as part of monitor data via second interface 104.

The monitor device 100 is configured to obtain ostomy data from the base plate coupled to the first interface 102. The ostomy data may be stored in the memory 106 and/or processed in the processor 101 in order to obtain parameter data.

Figure 3:
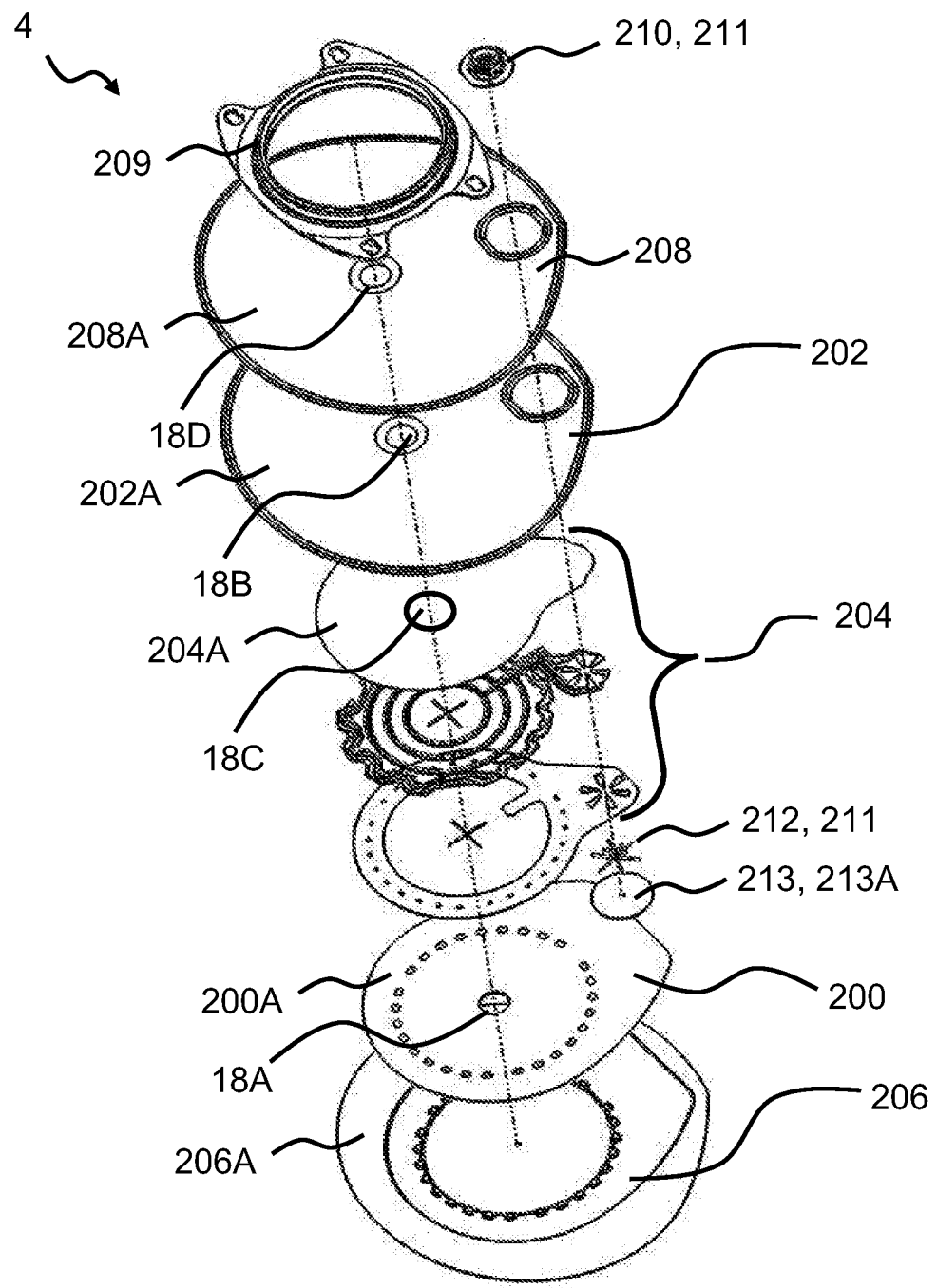
FIG. 3 is an exploded view of a base plate of an ostomy appliance.

FIG. 3 illustrates an exploded view of an exemplary base plate of an ostomy appliance. The base plate 4 comprises a first adhesive layer 200 with a stomal opening 18A. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202 with a stomal opening 18B. The base plate 4 comprises a plurality of electrodes arranged in an electrode assembly 204. The electrode assembly 204 is arranged between the first adhesive layer 200 and the second adhesive layer 202. The electrode assembly 204 comprises a support layer with stomal opening 18C and electrodes formed on a proximal surface of the support layer. The base plate 4 comprises a release liner 206 that is peeled off by the user prior to applying the base plate 4 on the skin. The base plate 4 comprises a top layer 208 with a stomal opening 18D and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the distal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

Figure 4:
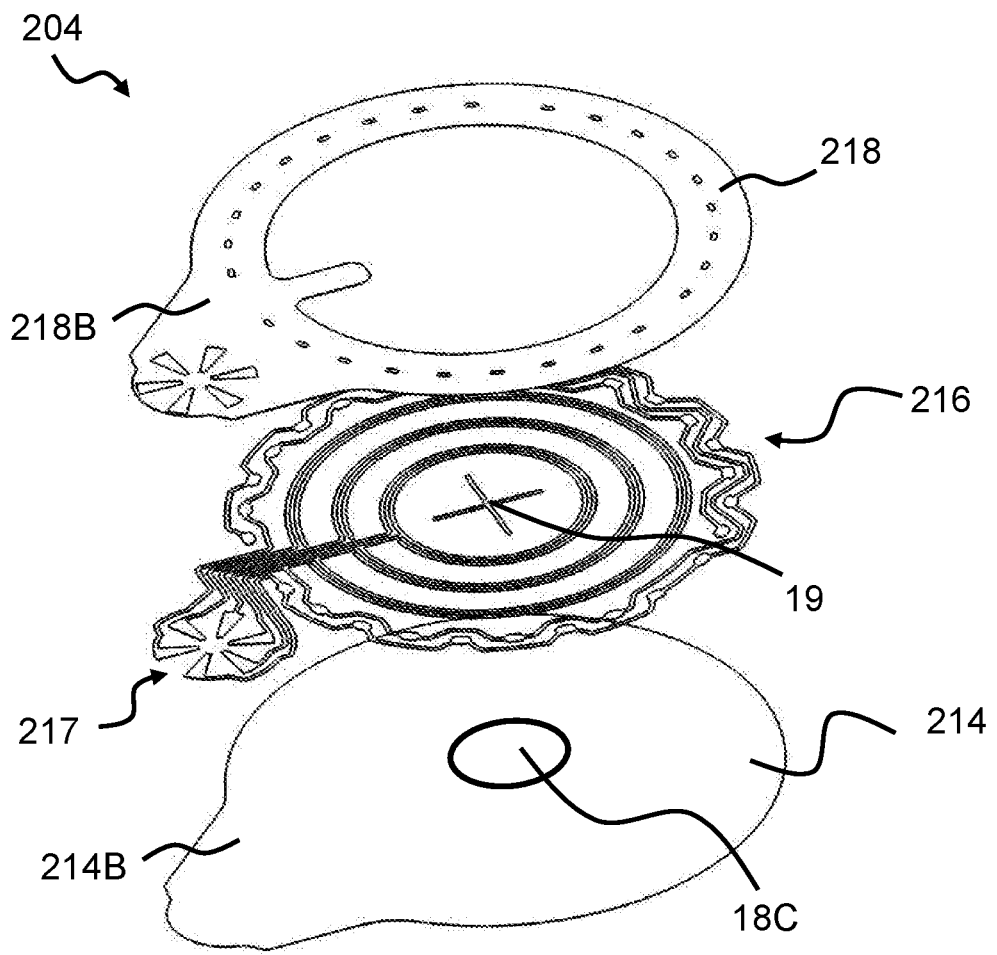
FIG. 4 is an exploded view of an exemplary electrode assembly.

FIG. 4 illustrates an exploded view of an exemplary electrode assembly 204 of a base plate. The electrode assembly 204 has a distal side 204A and a proximal side 204B. The electrode assembly 204 comprises a support layer 214 with proximal surface 214B and electrodes 216 arranged on the proximal side of the support layer 214 and including a ground electrode, a first electrode, a second electrode, a third electrode, a fourth electrode, and a fifth electrode, wherein each electrode has a respective connection part 217 for connecting the electrodes 216 to respective terminal elements of the monitor interface. The electrodes 216 are positioned and/or formed on a proximal side 214B of the support layer 214. Further, electrode assembly 204 comprises a masking element 218 with proximal surface 218B and configured to insulate electrode parts of electrodes 216 from the first adhesive layer of the base plate. The masking element 218 covers or overlap with parts of the electrodes 216 when seen in the axial direction.

Figure 5:
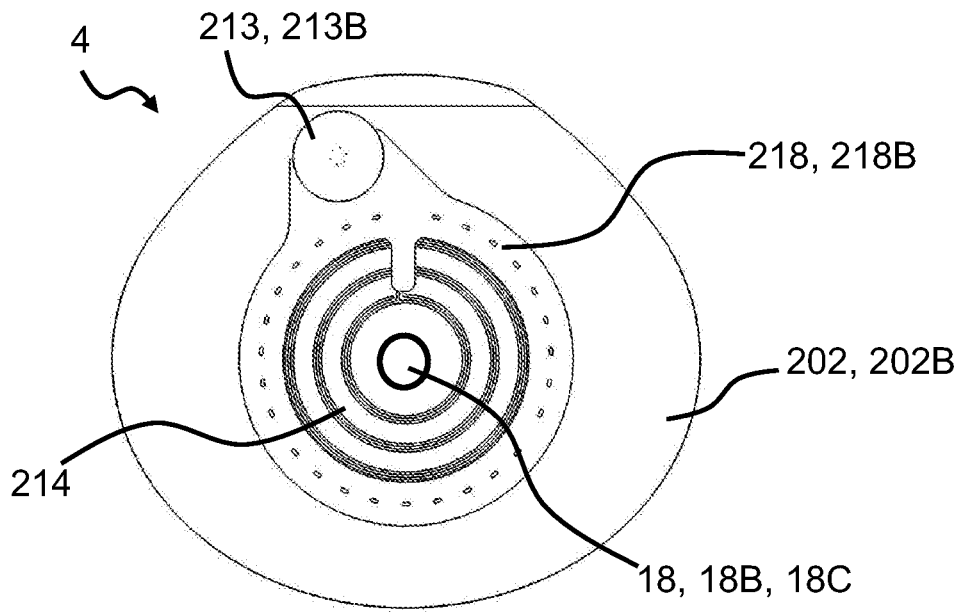
FIG. 5 is a proximal view of parts of a base plate.

FIG. 5 is a proximal view of proximal surfaces of base plate parts of the base plate without the first adhesive layer and the release liner. The base plate 4 comprises a first intermediate element 213 on the distal side of the electrode assembly, i.e. between the electrode assembly 204 and the first adhesive layer (not shown). The first intermediate element 213 covers the terminal elements of the base plate 4 when seen in the axial direction and protects the first adhesive layer from mechanical stress from the terminal elements of the base plate.

Figure 6:
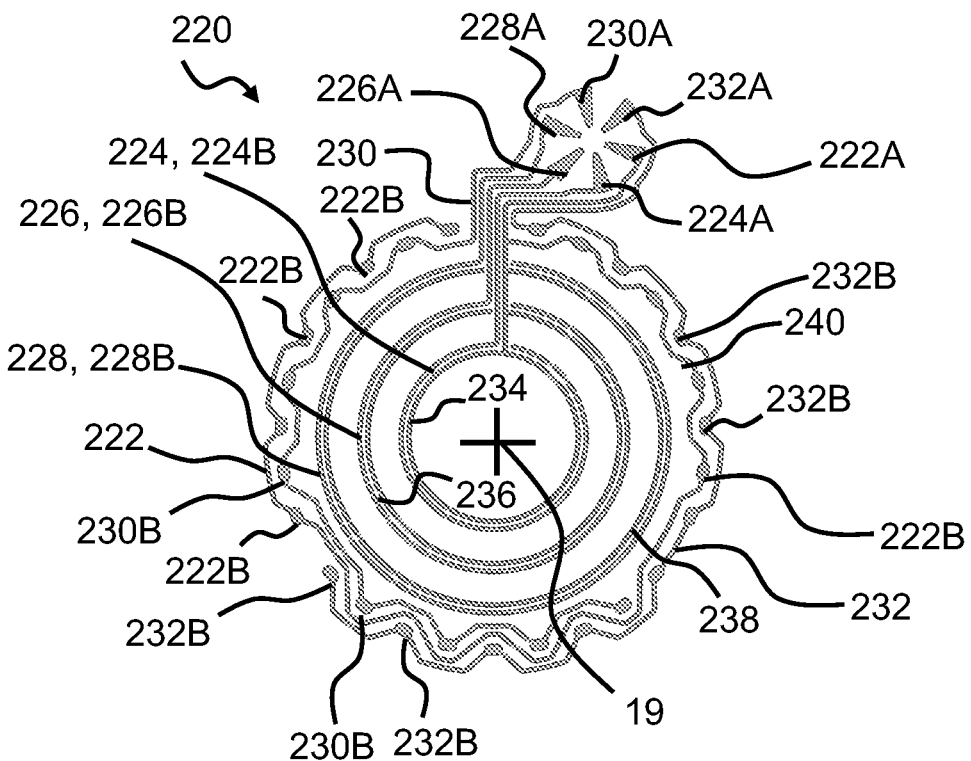
FIG. 6 is a distal view of an exemplary electrode configuration.

FIG. 6 is a distal view of an exemplary electrode configuration 220 of electrodes 216 of the electrode assembly 204. The electrode configuration 220/electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode 230 comprises fourth sensing parts 230B. The fifth electrode 232 comprises fifth sensing parts 232B.

The ground electrode 222 comprises a first electrode part 234 for forming a ground or reference for the first electrode 224. The ground electrode 222 comprises a second electrode part 236 for forming a ground or reference for the second electrode 226. The ground electrode 222 comprises a third electrode part 238 for forming a ground or reference for the third electrode 228. The masking element 218 is arranged proximal to the electrodes 222, 224, 226, 228 covering and insulating parts of the electrodes from the first adhesive and forming respective conductor parts of the electrodes 222, 224, 226, 228. The parts of the electrodes 222, 224, 226, 228 not covered by the masking element 219 contacts the first adhesive layer and form sensing parts 224B, 226B, 228B of electrodes 224, 226, 228, respectively. Further, the electrode parts 234, 236, 238 form sensing parts of the ground electrode 222.

The first sensing part 224B extends circularly at least 330 degrees around the stomal opening at a first radial distance R1 from the center point 19. The first radial distance R1 may be around 14 mm. In one or more embodiments, the first radial distance R1 may be around 13 mm, such as 12.5 mm. The first electrode part 234 is arranged on the inside of the first sensing part (i.e. closer to the center point) and extends circularly at least 330 degrees around the stomal opening at a first ground distance RG1 from the first sensing part (radially from the center point). The first ground distance RG1 between sensing part of first electrode and first electrode part is about 1 mm.

The second sensing part 226B extends circularly at least 330 degrees around the stomal opening at a second radial distance R2 from the center point 19. The second radial distance R2 may be around 18 mm. In one or more embodiments, the second radial distance R2 may be 17 mm. The second electrode part 236 is arranged on the inside of the second sensing part 226B (i.e. closer to the center point) and extends circularly at least 330 degrees around the stomal opening at a second ground distance RG2 from the second sensing part 226B (radially from the center point). The second ground distance RG2 between sensing part of second electrode and second electrode part is about 1 mm.

The third sensing part 228B extends circularly at least 330 degrees around the stomal opening at a third radial distance R3 from the center point 19. The third radial distance R3 is about 26 mm. In one or more embodiments, the third radial distance R3 is 21 mm. The third electrode part 238 is arranged on the inside of the third sensing part 228B (i.e. closer to the center point) and extends circularly at least 330 degrees around the stomal opening at a third ground distance RG3 from the third sensing part 228B (radially from the center point). The third ground distance RG3 between sensing part of third electrode and third electrode part is about 1 mm.

The ground electrode 222 comprises a fourth electrode part 240 for forming a ground or reference for the fourth electrode 230 and the fifth electrode 232. The fourth electrode part 240 of the ground electrode 222 extends at least 300 degrees around the stomal opening and comprises ground sensing parts 222B. The fourth sensing parts 230B, fifth sensing parts 232B, and ground sensing parts of the fourth electrode part 240 are circularly distributed around the center point 19 at a leakage radius from the center point (such as a leakage radius R5 which may be around 32 mmm from the center point). The fourth sensing parts 230B, fifth sensing parts 232B, and ground sensing parts of the fourth electrode part may have a radial extension larger than 1.0 mm, such as in the range from 1.5 mm to 3.0 mm, e.g. about 2.0 mm. The fourth sensing parts 230B, fifth sensing parts 232B, and ground sensing parts of the fourth electrode part 240 may have a circumferential extension (perpendicular to the radial extension) larger than 1.0 mm, such as in the range from 2.5 mm to 5.0 mm, e.g. about 3.5 mm.

Figure 7:
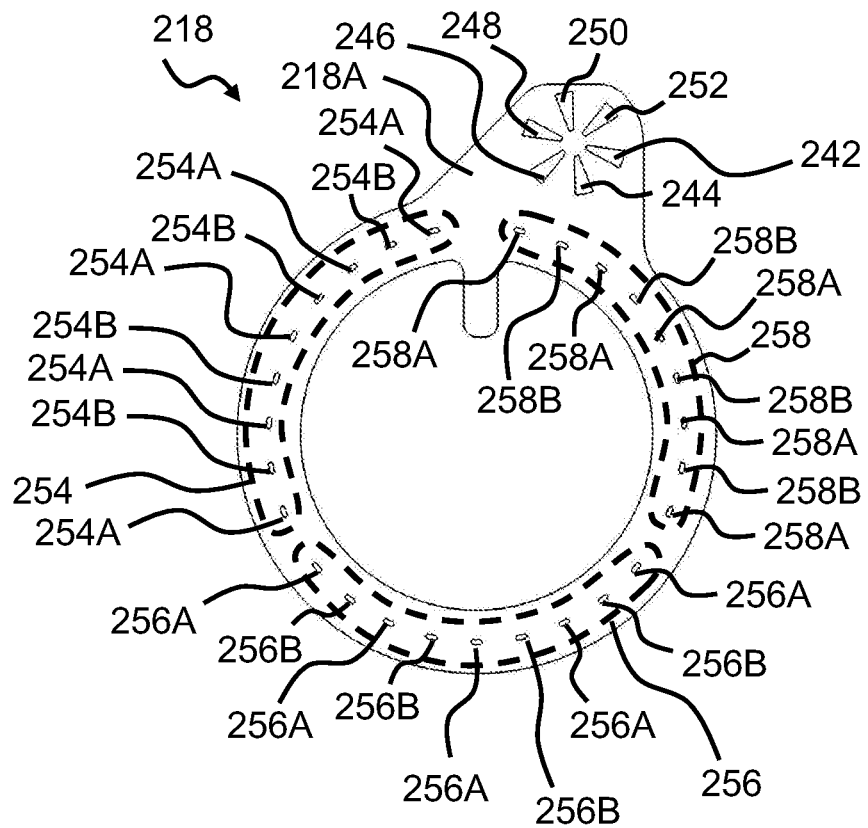
FIG. 7 is a distal view of an exemplary masking element.

FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode 222 and/or a part of the fourth electrode 230. The primary sensor point openings 254 comprise, in the illustrated exemplary masking element, five primary first sensor point openings 254A each configured to overlap a part of the ground electrode 222. The primary sensor point openings 254 comprise, in the illustrated exemplary masking element, four primary second sensor point openings 254B each configured to overlap a part of the fourth electrode 230. The sensor point openings comprise secondary sensor point openings shown within dotted line 256, each second sensor point opening configured to overlap a part of the fourth electrode 230 and/or a part of the fifth electrode 232. The secondary sensor point openings 256 comprise, in the illustrated exemplary masking element, five secondary first sensor point openings 256A each configured to overlap a part of the fifth electrode 232. The secondary sensor point openings 256 comprise, in the illustrated exemplary masking element, four secondary second sensor point openings 256B each configured to overlap a part of the fourth electrode 230. The sensor point openings comprise tertiary sensor point openings shown within dotted line 258, each tertiary sensor opening configured to overlap a part of the fifth electrode 232 and/or a part of the ground electrode 222. The tertiary sensor point openings 258 comprise, in the illustrated exemplary masking element, five tertiary first sensor point openings 258A each configured to overlap a part of the fifth electrode 232. The tertiary sensor point openings 258 comprise, in the illustrated exemplary mask-ing element, four tertiary second sensor point openings 258B each configured to overlap a part of the ground electrode 222.

Figure 8:
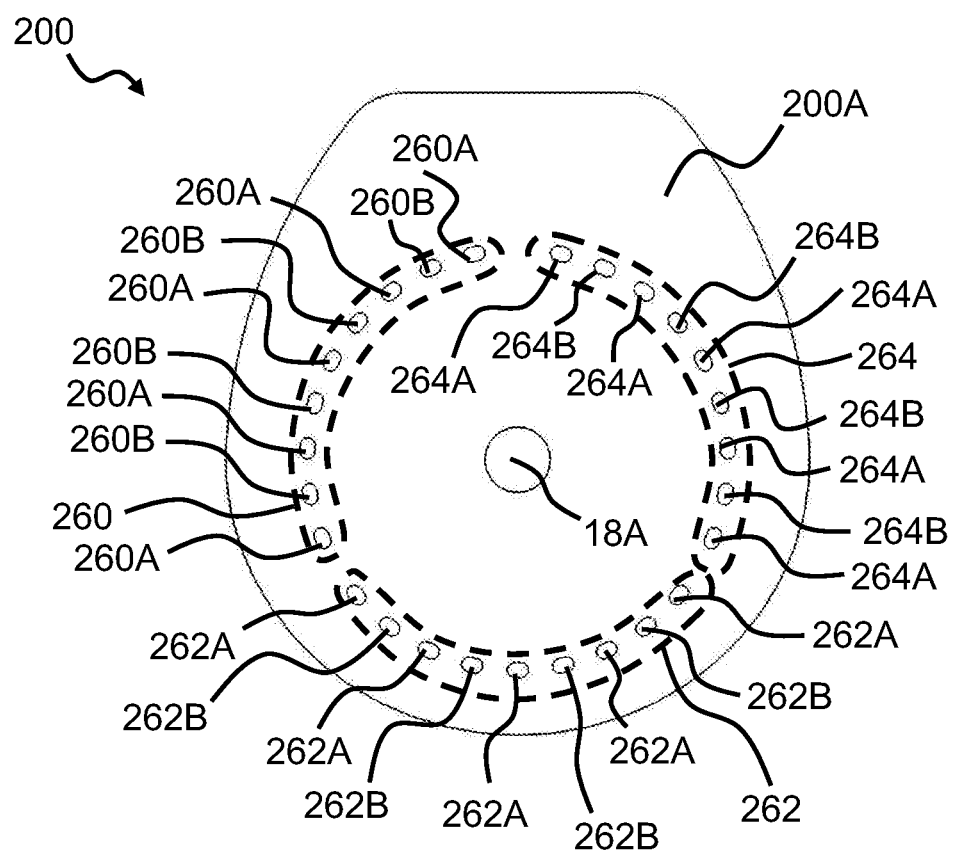
FIG. 8 is a distal view of an exemplary first adhesive layer.
Figure 9:
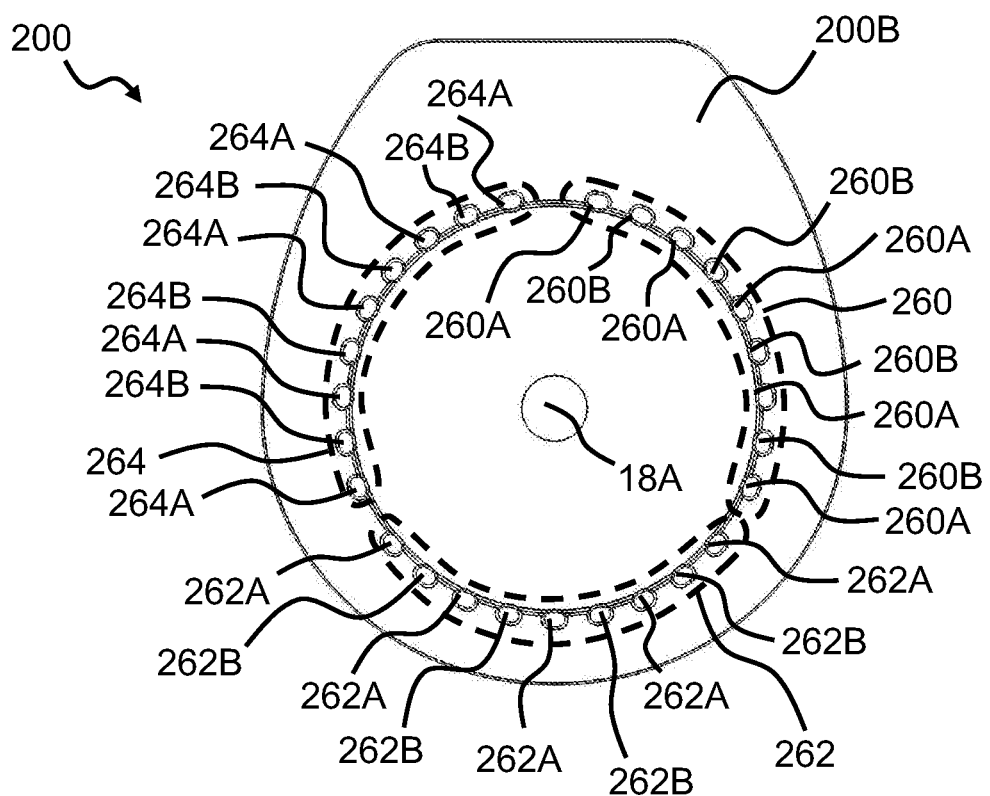
FIG. 9 is a proximal view of the first adhesive layer of FIG. 8.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings comprise, in the illustrated exemplary first adhesive layer, five primary first sensor point openings 260A each configured to overlap a part of the ground electrode 222. The primary sensor point openings comprise, in the illustrated exemplary first adhesive layer, four primary second sensor point openings 260B each configured to overlap a part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings comprise, in the illustrated exemplary first adhesive layer, five secondary first sensor point openings 262A each configured to overlap a part of the fifth electrode 232. The secondary sensor point openings comprise, in the illustrated exemplary first adhesive layer, four secondary second sensor point openings 262B each configured to overlap a part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings comprise, in the illustrated exemplary first adhesive layer, five tertiary first sensor point openings 264A each configured to overlap a part of the fifth electrode 232. The tertiary sensor point openings comprise, in the illustrated exemplary first adhesive layer, four tertiary second sensor point openings 264B each configured to overlap a part of the ground electrode 222. FIG. 9 is a proximal view of the first adhesive layer of FIG. 8.

Figure 10:
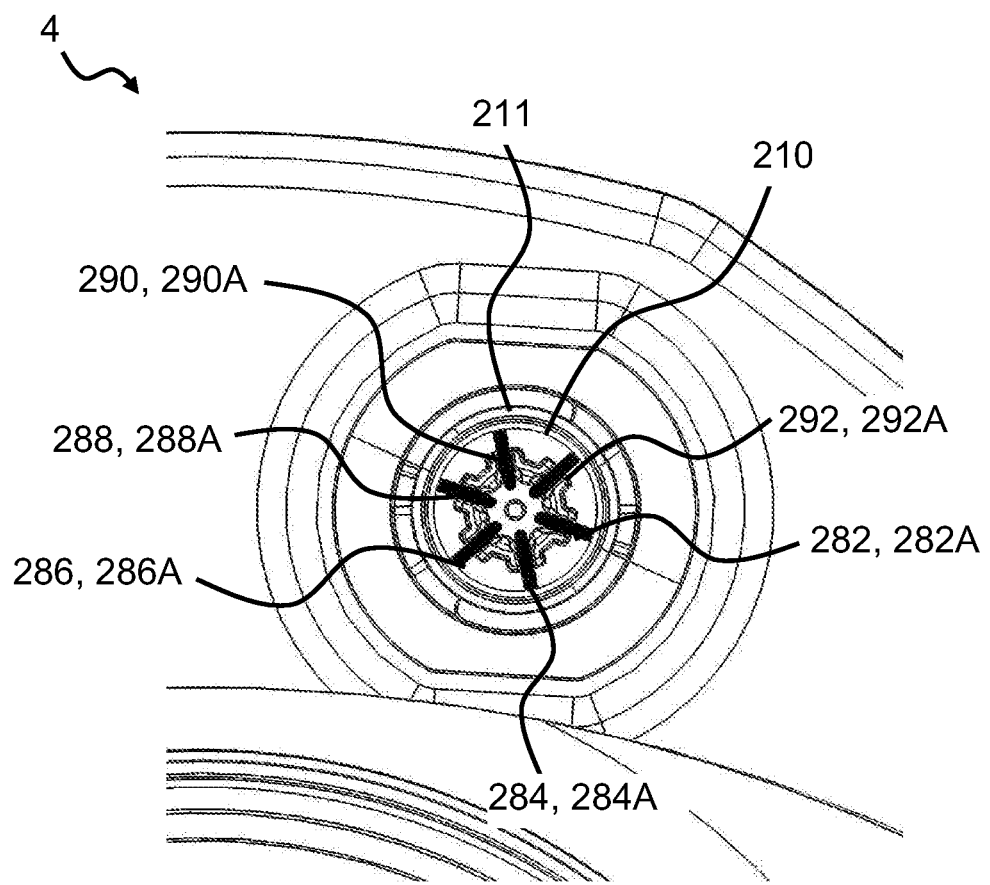
FIG. 10 is a distal view of a part of the base plate including monitor interface.

FIG. 10 is a more detailed distal view of a part of the base plate 4. Monitor interface of the base plate comprises the first connector 211. The first connector 211 comprises coupling part 210 configured to releasably couple the monitor device to the base plate and thus forming a releasable coupling. The first connector 211/monitor interface comprises a plurality of terminals formed by respective terminal elements for forming respective electrical connections with respective terminals of the monitor device.

The plurality of terminals of the first connector 211/ monitor interface comprises a ground terminal element 282 forming a ground terminal 282A, a first terminal element 284 forming a first terminal 284, a second terminal element 286 forming a second terminal 286A, and optionally a third terminal element 288 forming a third terminal 288A. The monitor interface optionally comprises a fourth terminal element 290 forming a fourth terminal 290A and/or a fifth terminal element 292 forming a fifth terminal 290. The terminal elements 282, 284, 286, 288, 290, 292 contact respective connection parts 222A, 224A, 226A, 228A, 230a, 232A of electrodes 222, 224, 226, 228, 230, 232.

The position of the first connector on the base plate, the number of terminals and the position of the terminals in the coupling part may be adapted to the electrode configuration used in the electrode assembly of the base plate.

Figure 11A:
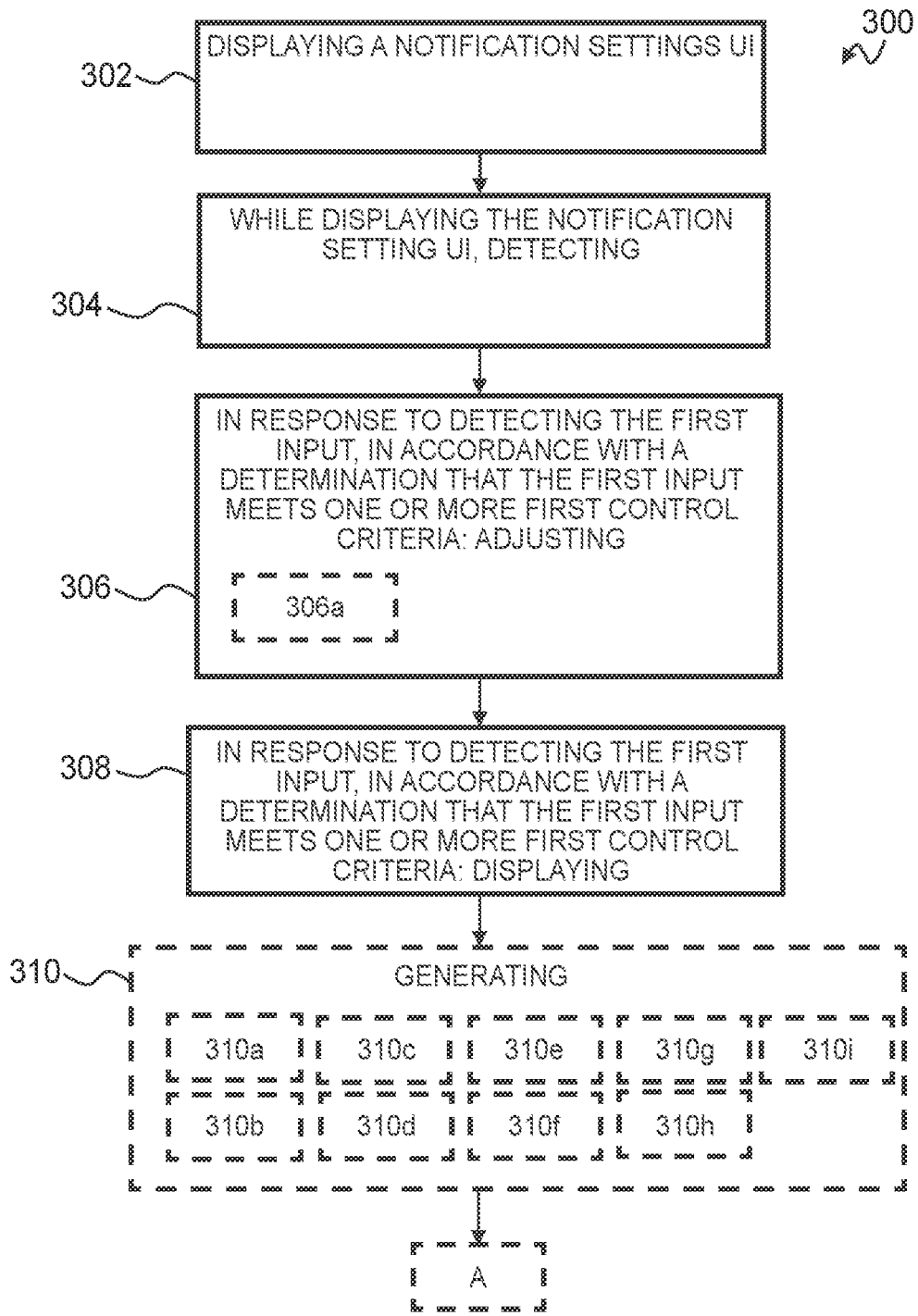
FIGS. 11a-b are flow charts illustrating an exemplary method performed in an accessory device.
Figure 11B:
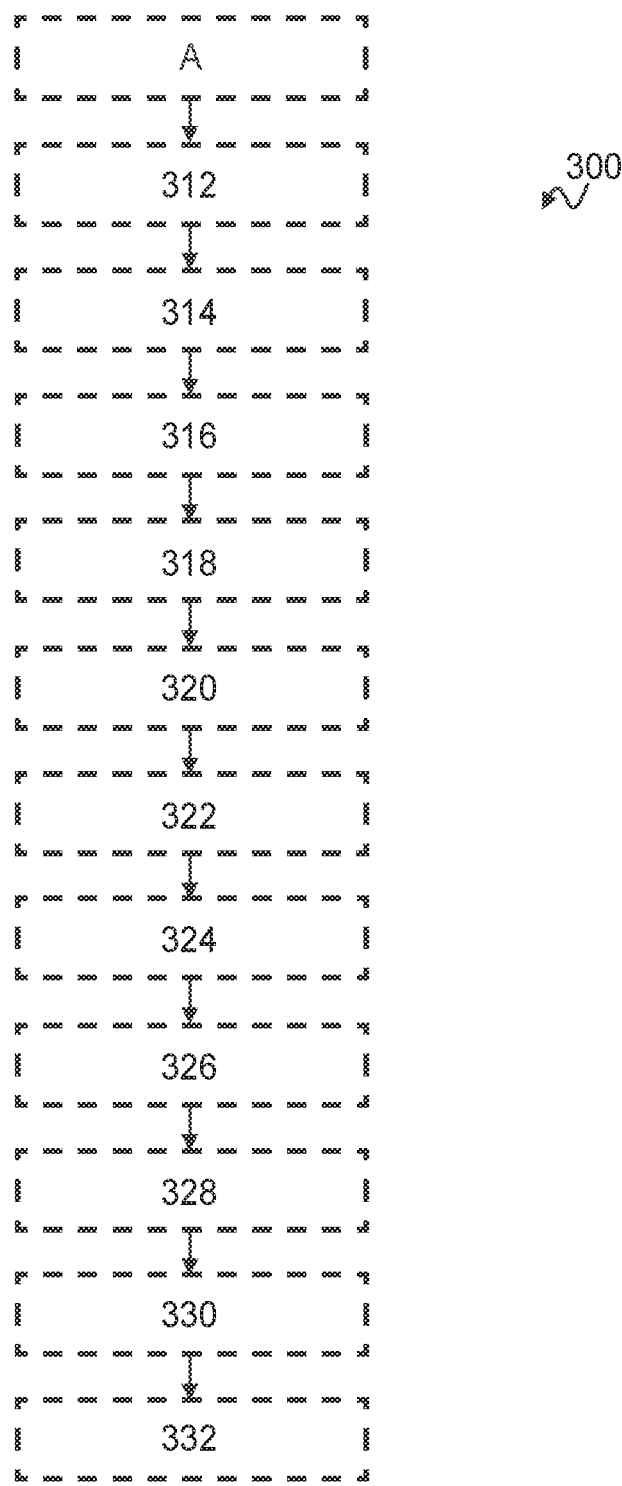

FIG. 11a-b shows a flow chart illustrating an exemplary method 300 performed in an accessory device. The method 300 is performed for configuring notifications, e.g. configuring ostomy notification, e.g. adjusting notification setting parameters, such as for setting ostomy notifications, e.g. notifications of an ostomy user application (e.g. user application for monitoring a base plate of the ostomy appliance). The accessory device comprises an interface configured to communicate with one or more devices of an ostomy system. The interface comprises a display. The ostomy system comprises a monitor device, and/or an ostomy appliance configured to be placed on a skin surface of a user, wherein the ostomy appliance comprises the base plate.

The method comprises displaying 302, on the display, a notification settings user interface comprising one or more control objects including a first control object (e.g. one or more control user interface objects including a first control user interface object). The notification setting parameters may comprise a frequency of notification, a time to notify, a recurrence, and/or a time to change ostomy appliance. A time to notify is a time period where a notification is to be generated and displayed.

The method comprises while displaying the notification settings user interface, detecting 304, e.g. by contact, a first input directed to the first control object. For example, detecting 304, by contact, a first input directed to the first control object may comprise detecting a touch input directed to the first control object. For example, detecting a first input directed to the first control object may comprise detecting an input using an input device (e.g. a keyboard) in an input field of the first control object.

The method may comprise: in response to detecting the first input, determining whether the first input meets one or more first control criteria. The method comprises: in response to detecting the first input, in accordance with a determination that the first input meets one or more first control criteria: adjusting 306, based on the detected first input, a first notification setting parameter that corresponds to the first control object. For example, adjusting 306, based on the detected first input, a first notification setting parameter that corresponds to the first control object comprises controlling (e.g. toggling, gradually changing) the first notification setting parameter according to the detected first input.

The method comprises displaying 308 an updated first control object in the notification settings user interface, e.g. according to the adjusting.

The first input may comprise a touch (e.g. a tap, a force touch, a long press), and/or a movement of contact (e.g. a swipe gesture, e.g. for toggling). The movement on contact may be detected by a touch sensitive surface, e.g. by a touch sensitive display. The first input may comprise a lift off, wherein a lift off is a detection of absence of touch on the touch sensitive surface following the detection of a contact. The first input may comprise a touch, and a movement followed by a lift off. Determining a lift off may comprise detecting absence of touch on the touch sensitive surface after having detected a touch (e.g. a discontinuation of contact in the detected touch). Detecting the first input may comprise detected a touch, and after detecting a touch, detecting absence of touch on the touch sensitive surface.

It is seen as an advantage of the disclosed methods and accessory devices that they permit customizing the notifications communicating the dynamic internal of the ostomy appliance to a user, which supports the user in coordinating the use of the ostomy appliance with the planning of daily life activities. The disclosed setting of ostomy notifications allows adjusting notifications to user needs, such as privacy needs, comfort needs, security needs, hygiene needs.

The one or more first control criteria may comprise a primary criterion that is met when a characteristic feature of the first input exceeds a threshold during the first input. The one or more first control criteria may comprise a primary criterion that is met when a characteristic feature of the contact exceeds a threshold during the first input. The characteristic feature of the contact may comprise intensity of contact (deep press, light press), magnitude of movement (distance travelled, speed), a duration of input.

Adjusting 306, based on the detected first input, a first notification setting parameter may comprise adjusting 306a, based on the characteristic feature of the detected first input, a first notification setting parameter.

The method may comprise generating 310, based on the adjusted notification setting, one or more notifications including a first notification. The first notification is displayed as a user interface object notifying the user of the operating state of the base plate. The first notification may be displayed as part of a widget, such as a widget displayed in a widget user interface screen.

Generating 310, based on the adjusted notification setting, the one or more notifications may comprise obtaining 310a monitor data from the one or more devices, obtaining 310b context data. Generating 310, based on the adjusted notification setting, the one or more notifications may comprise determining 310c one or more operating states of the ostomy appliance based on the monitor data and the context data. An operating state is indicative of future adhesive performance of the ostomy appliance. Generating 310, based on the adjusted notification setting, the one or more notifications may comprise generating 310d the one or more notifications based on the adjusted first notification setting parameter and the one or more operating states, and optionally a predicted future operating state.

Generating 310d the one or more notifications based on the adjusted first notification setting parameter and the one or more operating states may comprise determining 310e whether at least one of the one or more operating states meets one or more notification criteria. Generating 310d the one or more notifications based on the adjusted first notification setting parameter and the one or more operating states may comprise in accordance with the determination that at least one of the one or more operating states meets one or more notification criteria: generating 310f the one or more notifications including the first notification based on the adjusted notification setting; and displaying 310g the first notification on the display, e.g. on the display of the accessory device.

The one or more operating states may comprise at least one of: a wear time, a quality of adhesion, and a moisture pattern representation. Wear time may comprise remaining wear time.

Obtaining 310b the context data may comprise obtaining the context data from a second application different from the ostomy user application. For example, the second application comprises a calendar application, a weather application, a health application, a sports application, an activity tracker application, a photo application, a camera, and/or a medical application. Obtaining 310b the context data may comprise obtaining the context data comprising calendar data from a calendar application installed on the accessory device. Calendar data comprises date, time, calendar events including event date, event start time, event end time, event recurrence, event location, event attendees, etc. Generating 310, based on the adjusted first notification setting parameter, one or more notifications may comprise generating 310h the one or more notifications based on the adjusted first notification setting parameter and the calendar data. The method 300 may comprise deriving one or more regular events not derived from the calendar application, such as commuting, going up and down stairs, walking dog etc. Obtaining 310b the context data may comprise obtaining the context data comprising location data, e.g. derived from location sensor data, derived from connectivity data.

Generating 310, based on the adjusted first notification setting parameter, one or more notifications comprises generating 310i the one or more notifications based on the adjusted first notification setting parameter and location data. The notification thereby derived may be based on location of the accessory device with respect to locations of one or more changing rooms. For example, the processor of the accessory device may be configured to generate the one or more notifications based on the location data characterizing a region or country of residence. As discussed in connection with FIG. 17, it is noted that various regions and countries have various routines and recommendations to support optimal use of an ostomy appliance. For example, in regions of Europe, it may be indicated to the user that an ostomy appliance with a base plate as disclosed herein is an optimal state (corresponding to a first operating state) when the radial thickness of the whitening ring is between 0-15 mm (for a user not in compliance with a preferred use), such as between 0-7 mm (for a user in compliance with a preferred use), such as between 0-5 mm (recommended by a nurse).

For example, in Europe, it may be indicated to the user that an ostomy appliance with a base plate as disclosed herein is in suboptimal state (corresponding to a second operating state) and thereby indicate a consideration to change the base plate when the radial thickness of the whitening ring is such as between 5-10 mm (recommended by a nurse), between 7 mm and 10 mm (for a user in compliance with a preferred use), and/or between 15 mm and 30 mm (for a user not in compliance with a preferred use).

For example, in Europe, it may be indicated to the user that an ostomy appliance with a base plate as disclosed herein is in a poor state (corresponding to a third operating state) and indicate a request to change the base plate when the radial thickness of the whitening ring is more than 10 mm (recommended by a nurse), such as more than 15 mm (for a user in compliance with a preferred use), such as more than 30 mm (for a user not in compliance with a preferred use).

For example, in other regions (e.g. America), it may be indicated to the user that an ostomy appliance with a base plate as disclosed herein is an optimal state (corresponding to a first operating state) when the radial thickness of the whitening ring is between 0-20 mm (for a user not in compliance with a preferred use), such as between 0-10 mm (for a user in compliance with a preferred use), such as between 0-10 mm (recommended by a nurse).

For example, in other regions (e.g. America), it may be indicated to the user that an ostomy appliance with a base plate as disclosed herein is in suboptimal state (corresponding to a second operating state) and thereby indicate a consideration to change the base plate when the radial thickness of the whitening ring is such as between 10 mm and 20 mm (recommended by a nurse), between 10 mm and 20 (for a user in compliance with a preferred use), and/or between 20 mm and 40 mm (for a user not in compliance with a preferred use).

For example, in other regions (e.g. America), it may be indicated to the user that an ostomy appliance with a base plate as disclosed herein is in a poor state (corresponding to a third operating state) and indicate a request to change the base plate when the radial thickness of the whitening ring is more than 20 mm (recommended by a nurse), such as more than 20 mm (for a user in compliance with a preferred use), such as more than 40 mm (for a user not in compliance with a preferred use).

The disclosed methods, and accessory devices allow to accommodate the regional preferences of user in their use of the ostomy appliance so as to provide appropriate notifications based on e.g. current operating state and/or a future operating state accordingly.

Displaying 310g the one or more notifications including the first notification may comprise displaying the one or more notifications including the first notification on a locked screen. Displaying 310g the one or more notifications including the first notification may comprise displaying the one or more notifications including the first notification on an unlocked screen.

In one or more exemplary methods, when the accessory device is in a locked state, the method 300 comprises detecting 312 an authentication input to unlock the device; in response to detecting the authentication input to unlock the device, verifying 314 the authentication input; unlocking 316 the accessory device in accordance with successful verification of the authentication input; and in response to unlocking of the accessory device, in accordance with successful verification of the authentication input, displaying 318 a first user interface including the first notification (e.g. overlaid on the first user interface). The authentication input may comprise a biometric input (e.g. face recognition, iris scanning and recognition, gaze detection, fingerprint detection), passcode.

The method 300 may comprises in accordance with unsuccessful verification of the authentication input, forgoing the displaying of the first notification in a first user.

In one or more exemplary methods, the method 300 comprises detecting 320 a biometric input, in response to detecting the biometric input, verifying 322 the biometric input; in accordance with successful verification of the biometric input, displaying the one or more notifications including the first notification comprises displaying 324 a long version of the first notification; in accordance with unsuccessful verification of the biometric input, displaying the one or more notifications including the first notification comprises displaying 326 a short version of the first notification. Displaying 310g the one or more notifications including the first notification comprises for example displaying, on the display, the first notification indicative of one or more operating states (e.g. on the lock screen and/or on the home screen of the accessory device).

In one or more exemplary methods, the method 300 comprises detecting 328 a second input selecting the first notification; in response to detecting the second input, opening 330 the ostomy user application. When the display is a touch sensitive display, the second user input may comprise a contact on the touch sensitive display.

In one or more exemplary methods, the method 300 comprises in response to opening the ostomy user application, displaying 332 a second user interface comprising a third user interface object representing the current operating state of the ostomy appliance and a fourth user interface object representing the one or more future operating states of the ostomy appliance.

Figure 12:
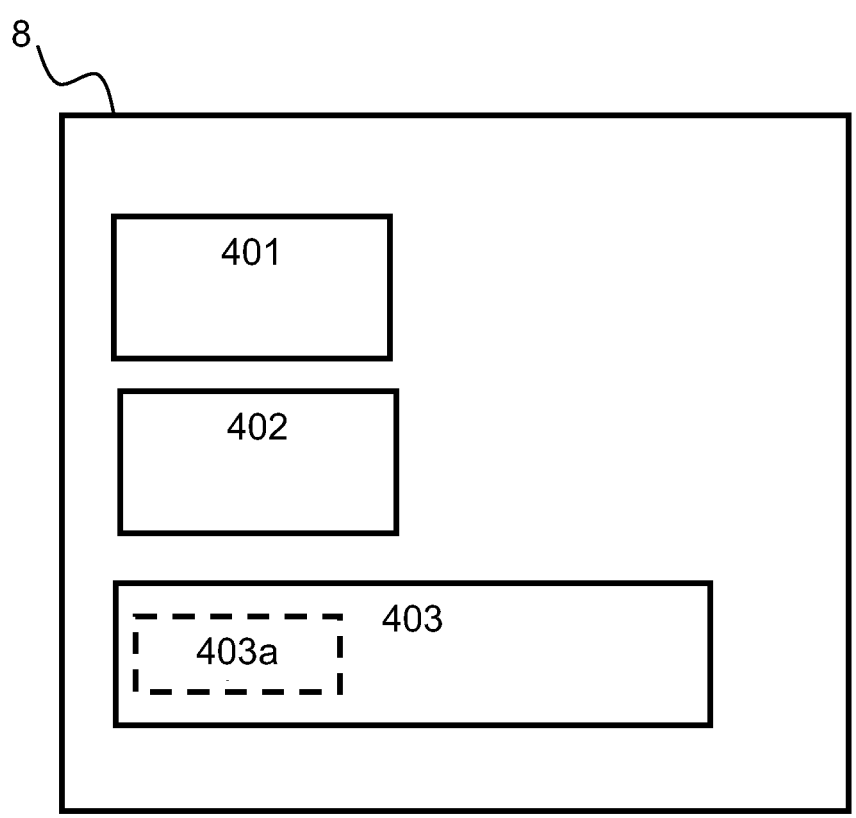
FIG. 12 is a block diagram illustrating an exemplary accessory device according to this disclosure.

FIG. 12 is a block diagram illustrating an exemplary accessory device 8 according to the present disclosure. The accessory device 8 forms part of an ostomy system and is capable of monitoring operating states of a base plate of an ostomy appliance to be placed on a user's skin, in particular of controlling notification settings related to the operating states.

The accessory device 8 comprises a memory 401; a processor 402 coupled to the memory 401; and an interface 403 coupled to the processor 402.

The interface 403 is configured to communicate with one or more devices of the ostomy system. The one or more devices comprise a monitor device disclosed herein, and/or an ostomy appliance configured to be placed on a skin surface of a user or on any additional seals. The ostomy appliance comprises a base plate. The base plate may comprise a first adhesive layer having a proximal side. During use, a proximal surface of the first adhesive layer adheres to the user's skin in the peristomal area and/or to additional seals, such as sealing paste, sealing tape and/or sealing ring. The base plate may comprise one or more electrodes configured to measure electrical properties of the first adhesive layer. The electrical properties may be indicative of a conductive path in the first adhesive layer, thereby indicative of the moisture level, and indicative of the condition of the ostomy appliance.

The interface 403 is configured to obtain monitor data from the one or more devices, such as to receive or retrieve the monitor data from the monitor device. The monitor data may be indicative of a condition of the ostomy appliance, such as a condition of a proximal side of a layer of the ostomy appliance (e.g. a first adhesive layer of the base plate) that is directed towards the skin surface.

The interface 403 comprises a display 403*a*, and a transceiver module. The display 403*a* is configured to display user interfaces including one or more user interface objects. The display 403*a* is configured to display a notification settings user interface comprising one or more control objects including a first control object, wherein the notification settings user interface is configured to adjust notification setting parameters of an ostomy user application.

The accessory device 8 (e.g. the interface 403 and the processor 402) is configured to: while displaying the notification settings user interface, detect, by contact, a first input directed to the first control object. The display 403*a* may be configured to detect contact, such as touch input, from the user. The display 403*a* may be a touch-sensitive display. The display 403*a* may comprise a touch-sensitive surface. The first input may comprise a touch (e.g. a tap, a force touch, a long press), and/or a movement of contact (e.g. a swipe gesture, e.g. for toggling).

The accessory device 8 (e.g. the interface 403 and the processor 402) is configured to determine whether the first input meets one or more first control criteria. The one or more first control criteria may comprise a primary criterion that is met when a characteristic feature of the first input exceeds a threshold during the first input. The one or more first control criteria may comprise a primary criterion that is met when a characteristic feature of the contact exceeds a threshold during the first input. The characteristic feature of the contact may comprise intensity of contact (deep press, light press), magnitude of movement (distance travelled, speed), a duration of input.

The accessory device 8 (e.g. the interface 403 and the processor 402) is configured to, in response to detecting the first input, in accordance with a determination that the first input meets one or more first control criteria: adjust, based on the detected first input, a first notification setting parameter that corresponds to the first control object; and to display an updated first control object in the notification settings user interface.

The accessory device 8 (e.g. the interface 403 and the processor 402) may be configured to adjust, based on the detected first input, a first notification setting parameter by adjusting, based on the characteristic feature of the detected first input, a first notification setting parameter.

The accessory device 8 (e.g. the interface 403 and the processor 402) may be configured to generate, based on the adjusted notification setting, one or more notifications including a first notification. The first notification is displayed as a user interface object notifying the user of the operating state of the base plate. The first notification may be displayed as part of a widget, such as a widget displayed in a widget user interface screen.

The accessory device 8 (e.g. the interface 403 and the processor 402) may be configured to generate, based on the adjusted notification setting, the one or more notifications by obtaining, via the interface 403, monitor data from the one or more devices, and obtaining context data.

The accessory device 8 (e.g. the interface 403 and the processor 402) may be configured to generate, based on the adjusted notification setting, the one or more notifications by determining one or more operating states of the ostomy appliance based on the monitor data and the context data. An operating state is indicative of future adhesive performance of the ostomy appliance.

The accessory device 8 (e.g. the interface 403 and the processor 402) may be configured to generate, based on the adjusted notification setting, the one or more notifications by generating the one or more notifications based on the adjusted first notification setting parameter and the one or more operating states.

The accessory device 8 (e.g. the interface 403 and the processor 402) may be configured to generate, based on the adjusted notification setting and the one or more operating states, the one or more notifications by determining whether at least one of the one or more operating states meets one or more notification criteria. The one or more operating states may comprise at least one of: a wear time, a quality of adhesion, and a moisture pattern representation.

The accessory device 8 (e.g. the interface 403 and the processor 402) may be configured to generate, based on the adjusted notification setting and the one or more operating states, the one or more notifications by, in accordance with the determination that at least one of the one or more operating states meets one or more notification criteria, generating the one or more notifications including the first notification based on the adjusted notification setting; and displaying the one or more notifications including the first notification on the display.

The processor 402 may be configured to obtain the context data from a second application different from the ostomy user application. For example, the second application comprises a calendar application, a weather application, a health application, a sports application, an activity tracker application, a photo application, a camera, and/or a medical application. To obtain the context data may comprise obtaining the context data comprising calendar data from a calendar application installed on the accessory device. Calendar data comprises date, time, calendar events including event date, event start time, event end time, event recurrence, event location, event attendees, etc. To generate, based on the adjusted first notification setting parameter, one or more notifications may comprise to generate the one or more notifications based on the adjusted first notification setting parameter and the calendar data. Due to activity (e.g. sports, bending, movement), experimental results have shown that the operating state may be affected negatively by a reducing factor ranging from 2 to 10 compared to when the user has no or little activity (e.g. a sedentary user), For example, a wear time may be reduced by a factor of 2 to 10 due to an extensive activity. For example, by identifying the user activity level, the future operating state may be determined by dividing the current operating state e.g. by a factor ranging from 2 to 10.

The accessory device may comprise a sensor unit comprising an accelerometer for sensing acceleration and provision of acceleration data to the processor.

Context data may comprise location data, e.g. derived from location sensor data, derived from connectivity data. To generate, based on the adjusted first notification setting parameter, one or more notifications may comprise generating the one or more notifications based on the adjusted first notification setting parameter and location data. The notification thereby derived may be based on location of the accessory device with respect to locations of one or more changing rooms.

The display 403a may be configured to display the one or more notifications including the first notification on a locked screen. The display 403a may be configured to display the one or more notifications including the first notification on an unlocked screen.

When the accessory device 8 is in a locked state, the accessory device 8 may be configured to detect, via the interface 403, an authentication input to unlock the accessory device; in response to detecting the authentication input to unlock the device, to verify the authentication input; to unlocking the accessory device 8 in accordance with successful verification of the authentication input. In response to unlocking of the accessory device 8, in accordance with successful verification of the authentication input, the display 403a may be configured to display a first user interface including the first notification (e.g. overlaid on the first user interface). The authentication input may comprise a biometric input (e.g. face recognition, iris scanning and recognition, gaze detection, fingerprint detection), passcode.

The accessory device 8 may be configured to detect a biometric input. In response to detecting the biometric input, the accessory device 8 may be configured to verify the biometric input. In accordance with successful verification of the biometric input, the display 403a may be configured to display the one or more notifications including the first notification by displaying a long version of the first notification. In accordance with unsuccessful verification of the biometric input, the display 403a may be configured to display the one or more notifications including the first notification by displaying a short version of the first notification. The first notification may be indicative of one or more operating states (e.g. on the lock screen and/or on the home screen of the accessory device).

The accessory 8 may be configured to detect a second input selecting the first notification; in response to detecting the second input, opening the ostomy user application. When the display is a touch sensitive display, the second user input may comprise a contact on the touch sensitive display.

In response to opening the ostomy user application, the display 403a may be configured to display a second user interface comprising a third user interface object representing the current operating state of the ostomy appliance and a fourth user interface object representing the one or more future operating states of the ostomy appliance.

Figure 13A:
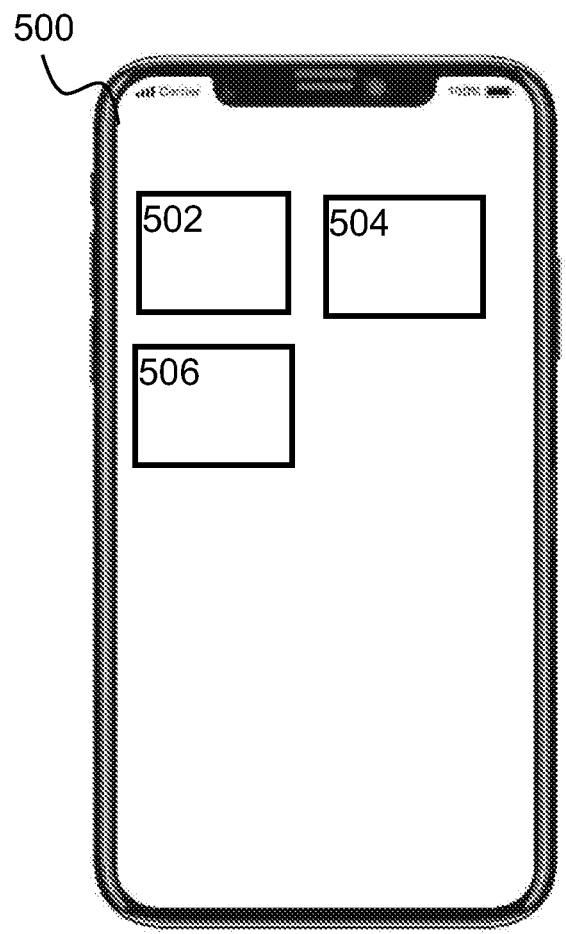
FIGS. 13a-c show exemplary user interfaces displayed on an exemplary accessory device for adjusting notifications related to a base plate of an ostomy appliance according to this disclosure.
Figure 13B:
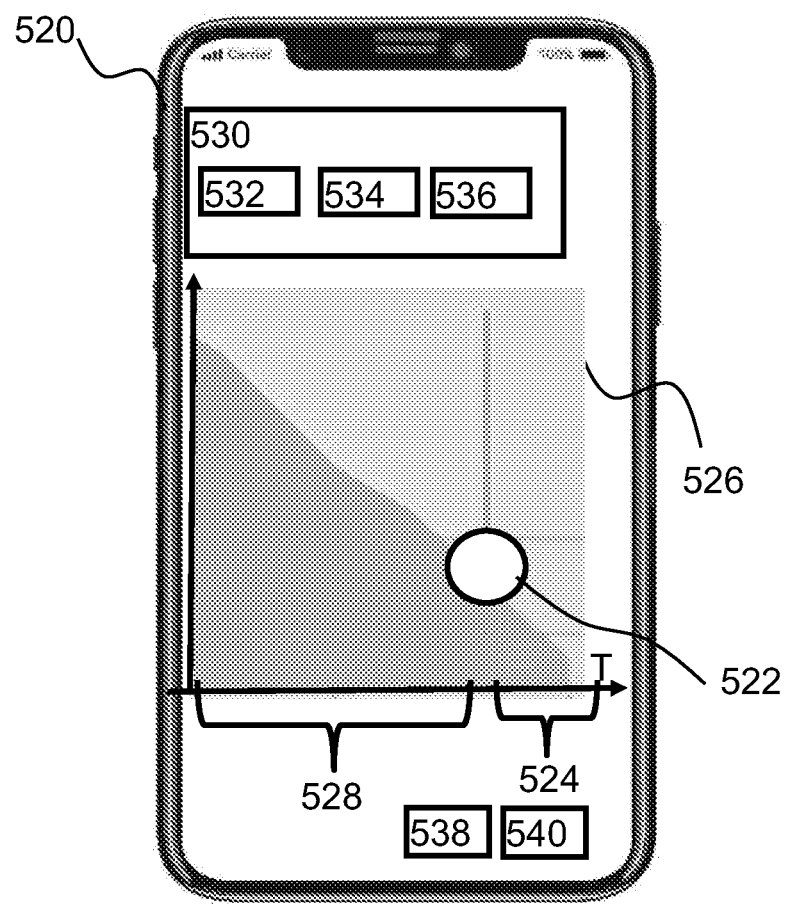
Figure 13C:
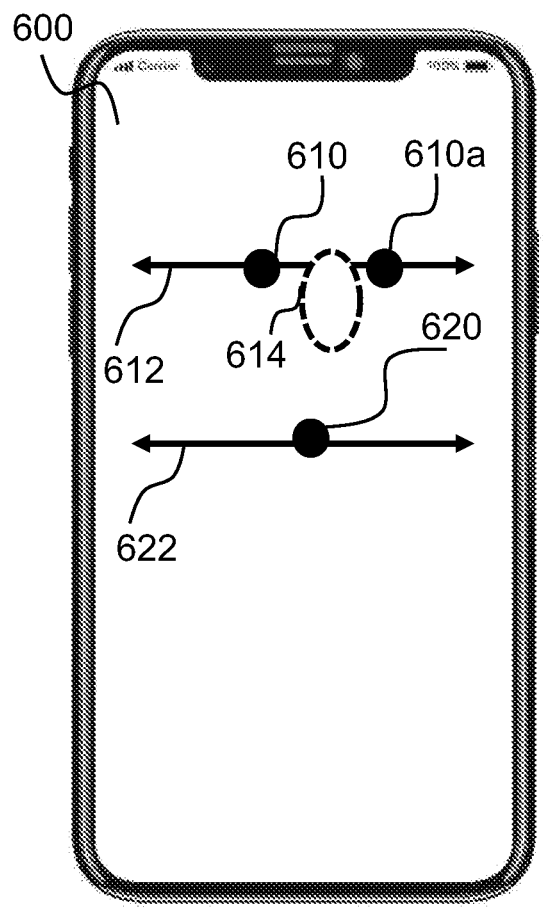

FIG. 13a-c show exemplary user interfaces displayed on an exemplary accessory device for adjusting notification settings related to a base plate of an ostomy appliance according to this disclosure, so as to notify the user of an ostomy appliance based on the operating state of a base plate disclosed herein.

FIG. 13a shows an exemplary first user interface 500.

First user interface 500 comprises a first primary user interface object 502 representing a first notification. First user interface 500 may comprise a plurality of user interface objects, e.g. a first primary user interface object 502 representing a first notification. The first user interface screen 500 may comprise additional user interface objects 504, 506, representing earlier notifications.

The first user interface 500 may comprise a lock screen of the accessory device (e.g. accessory device 8 of FIG. 1), and/or a home screen of the accessory device (e.g. accessory device 8 of FIG. 1).

A first input selecting any of user interface objects 502, 504, and 506, may be detected by the accessory device (e.g. accessory device 8 of FIG. 1), and in response to detecting the first input, the accessory device (e.g. accessory device 8 of FIG. 1) launches or opens an ostomy user application, (e.g. an ostomy user application installed on the accessory device (e.g. accessory device 8 of FIG. 1)). For example, detection of first input that corresponds to selection any of user interface objects 502, 504, 506 triggers the launch and opening of the ostomy user application installed on the accessory device (e.g. accessory device 8 of FIG. 1), as shown in corresponding user interface of FIG. 13bc.

FIG. 13b shows an exemplary user interface, such as a second user interface 520. The second user interface 520 comprises a third user interface object 522 representing the current operating state of the ostomy appliance and a fourth user interface object 524 representing the one or more future operating states of the ostomy appliance.

The second user interface 520 comprises user interface object 526 representative of a graph of a function or of a set that provides user interface objects 528 representing previous operating states, third user interface object 522 representing the current operating state and fourth user interface object 524 representative of one or more future operating states over time T, e.g. over a time window comprising at least of part of an elapsed time prior to the current time, current time and a future time period after the current time. The graph comprises values indicative of operating states in the y-axis. The operating state may comprise wear time such as remaining wear time.

The second user interface 520 may comprise a user interface object 530 representing a summary status of the base plate comprising a wear time user interface object 532 and a recommendation user interface object 534. The wear time user interface object 532 may be an indicator of the wear time (e.g. elapsed or remaining wear time) for the presently worn ostomy appliance, such as the presently worn base plate. The wear time user interface object 532 may comprise a day indicator and an hour indicator (e.g. 2 Days and 15 h). The recommendation user interface object 534 may be a text prompt in the like of: "Your base plate is worn, Change is recommended," "Everything is fine, no problems detected".

The second user interface 520 comprising the second primary user interface object 522 representing the current operating state of the ostomy appliance and the second secondary user interface object 524 representing the future operating state is displayed in response to opening the ostomy user application.

The second user interface 520 may be seen as one of the user interface screen displayed by the ostomy user application.

The second primary user interface object 522 representing the current operating state of the ostomy appliance may have a graphical representation derived from the graphical representation of the first primary user interface object 502 (e.g. increased or decreased in size, resolution; providing more precise information regarding the respective operating states).

The second user interface 520 may comprise a user interface object 536 to access a notification settings interface of the user ostomy application.

The second user interface 520 may comprise a fifth user interface object 538 indicative of the connection between the monitor device and the base plate. The fifth user interface object 538 may indicate a connection state for the connection between the monitor device and the base plate (such as connected, not connected, searching, failed connection).

The second user interface 520 may comprise a sixth user interface object 540 indicative of battery status of the monitor device. The sixth user interface object 540 may indicate a remaining battery time, and/or a remaining battery percentage (e.g. state of charge).

FIG. 13*c* shows an exemplary notification settings user interface 600.

The notification settings user interface 600 comprises one or more control objects including a first control object 610 for adjusting a first notification setting parameter across a scale represented by user interface object 612, a second control object for adjusting a second notification setting parameter a scale represented by user interface object 622. The notification settings user interface 600 is configured to adjust notification setting parameters of an ostomy user application, including a first notification setting parameter, a second notification setting parameter, a third notification setting parameter, and/or a fourth notification setting parameter. The notification setting parameters may comprise a frequency of notification, a time to notify, a recurrence, and/or a time to change ostomy appliance. A time to notify is a time period where a notification is to be generated and displayed. The notification setting parameters may comprise an indicator of the user experience in using an ostomy appliance.

The scale represented by user interface object 612 may range from a lower range of the first notification setting parameter to a higher range of the first notification setting parameter, e.g. from a lower range of frequency of notification (e.g. once a day) to a higher range of frequency of notification (e.g. every 10 min), e.g. from a lower range of a time to notify (e.g. 5 min before) to a higher range of a time to notify (e.g. 2 h before), e.g. from a lower range of recurrence (e.g. once every 3 days) to a higher range of a time to notify (e.g. every hour), from a lower range of experience of the user (e.g. inexperienced in ostomy care) to a higher range of a time to notify (e.g. expert in ostomy care).

A first input directed to the first control object 610 or the second control object 620 detected may comprise a touch input directed to the first control object 610 or the second control object 620. In response to detecting the first input, the accessory device (e.g. accessory device 8 of FIG. 1) determines whether the first input meets one or more first control criteria (e.g. the first input 614 resulting in a movement of the first control object 610 on scale 612, as shown by updated first control object 610*a*). In response to detecting the first input, in accordance with a determination that the first input meets one or more first control criteria, the accessory device (e.g. accessory device 8 of FIG. 1) adjusts, based on the detected first input, a first notification setting parameter that corresponds to the first control object 610 or a second notification setting parameter that corresponds to the second control object 620.

Figure 14:
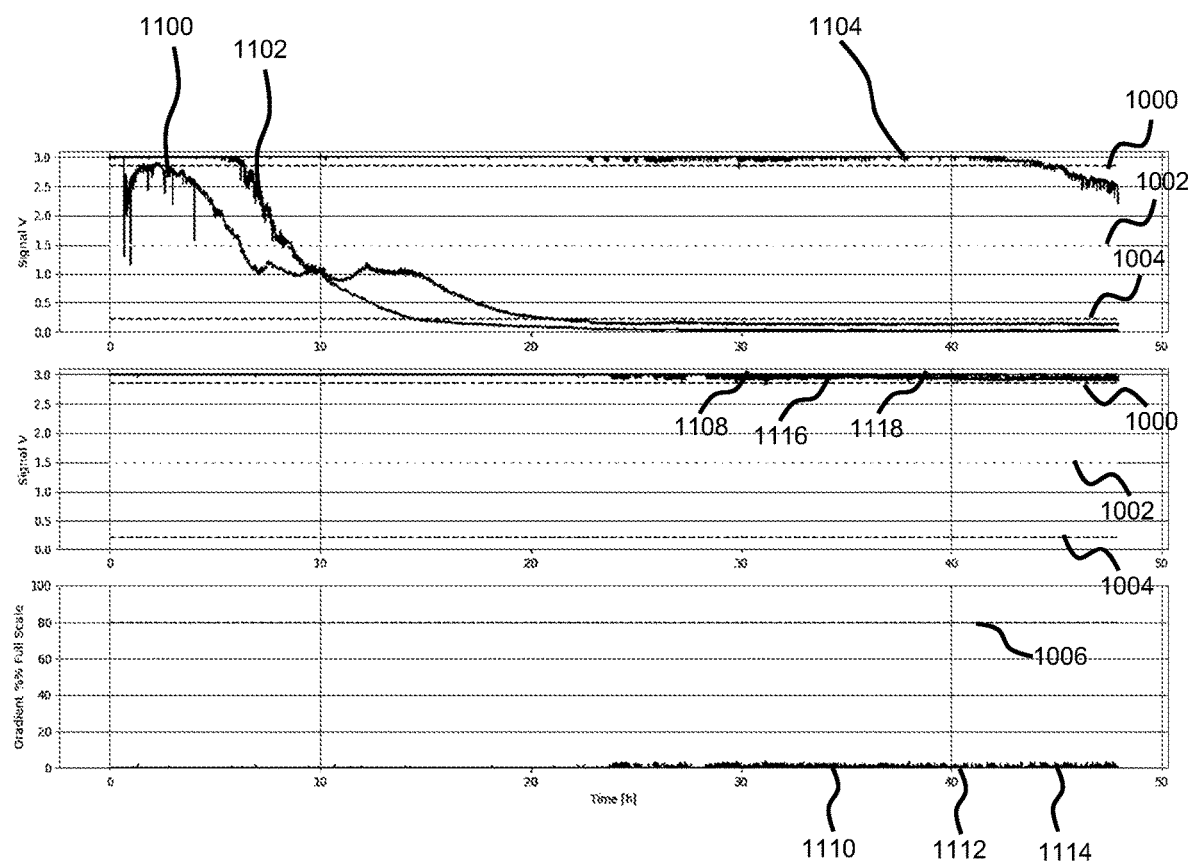
FIG. 14 is an exemplary graphical representation of parameter data as a function of time.

FIG. 14 shows an exemplary graphical representation of parameter data as a function of time. In this example, the parameter data in the y-axis is in Volts and time is in the x-axis. Curve 1100 shows, as a function of time, first parameter data indicative of voltage measured by the first electrode pair of the base plate. Curve 1102 shows, as a function of time, second parameter data indicative of voltage measured by the second electrode pair of the base plate. Curve 1104 shows, as a function of time, third parameter data indicative of voltage measured by the third electrode pair of the base plate. Curves 1108, 1116, 1118 show, as a function of time, fourth primary parameter indicative of voltage measured by the fourth electrode pair of the base plate, fourth secondary parameter indicative of voltage measured by the fourth electrode and the fifth electrode of the base plate, and fourth tertiary parameter indicative of voltage measured by the fifth electrode pair of the base plate respectively. Curves 1110, 1112, 1114 show, as a function of time, a gradient of fourth primary parameter indicative of voltage gradient measured by the fourth electrode pair of the base plate, a gradient of fourth secondary parameter indicative of voltage gradient measured by the fourth electrode and the fifth electrode of the base plate, and a gradient of fourth tertiary parameter indicative of voltage gradient measured by the fifth electrode pair of the base plate respectively. FIG. 14 shows the upper voltage threshold value represented as curve 1000, the medium voltage threshold value represented as curve 1002, the lower voltage threshold value represented as curve 1004, and curve 1006 is a gradient limit.

Curves 1108, 1116, 1118 as well as curves 1110, 1112, 1114 show that no moisture is detected at the proximal side of the first adhesive layer by the fourth electrode pair.

At a time less than 5 h, curve 1100 shows that moisture is detected by the first electrode pair as the first parameter data crosses the upper voltage threshold value while curve 1102 shows that moisture is not detected by the second electrode pair as the second parameter data has not crossed the upper voltage threshold value. At this stage, it is determined that the ostomy appliance is in a first operating state.

At time between 5 h and 10 h, curve 1102 shows that moisture is detected by the second electrode pair as the second parameter data crosses the upper voltage threshold value. At this stage, it is determined that the ostomy appliance is in a second operating state.

At time around 45 h, curve 1104 shows that moisture is detected by the third electrode pair as the third parameter data crosses the upper voltage threshold value. At this stage, it is determined that the ostomy appliance is in a third operating state.

Figure 15:
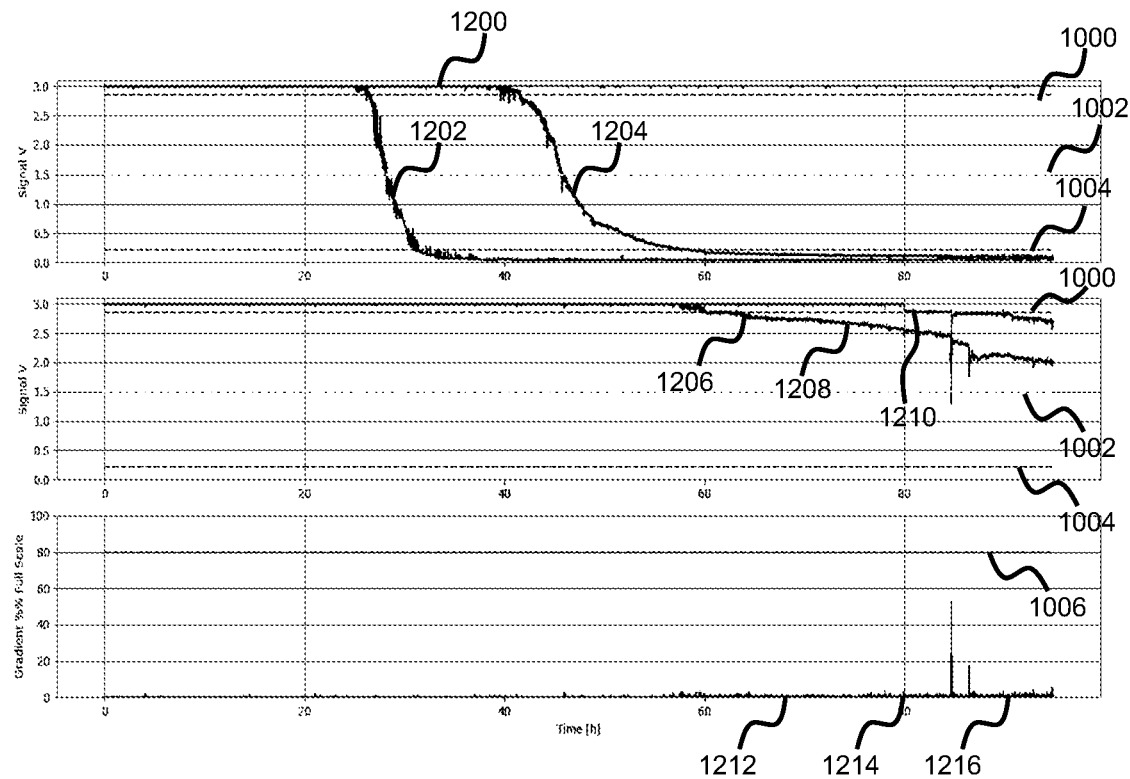
FIG. 15 is an exemplary graphical representation of parameter data as a function of time.

FIG. 15 shows an exemplary graphical representation of parameter data as a function of time. In this example, the parameter data in the y-axis is in Volts and time is in the x-axis. Curve 1202 shows, as a function of time, first parameter data indicative of voltage measured by the first electrode pair of the base plate. Curve 1204 shows, as a function of time, second parameter data indicative of voltage measured by the second electrode pair of the base plate. Curve 1200 shows, as a function of time, third parameter data indicative of voltage measured by the third electrode pair of the base plate. Curves 1206, 1208, 1210 show, as a function of time, fourth primary parameter indicative of voltage measured by the fourth electrode pair of the base plate, fourth secondary parameter indicative of voltage measured by the fourth electrode and the fifth electrode of the base plate, and fourth tertiary parameter indicative of voltage measured by the fifth electrode pair of the base plate respectively. Curves 1212, 1214, 1216 show, as a function of time, a gradient of fourth primary parameter indicative of voltage gradient measured by the fourth electrode pair of the base plate, a gradient of fourth secondary parameter indicative of voltage gradient measured by the fourth electrode and the fifth electrode of the base plate, and a gradient of fourth tertiary parameter indicative of voltage gradient measured by the fifth electrode pair of the base plate respectively. FIG. 15 shows the upper voltage threshold value represented as curve 1000, the medium voltage threshold value represented as curve 1002, the lower voltage threshold value represented as curve 1004, and curve 1006 represents a gradient limit.

Curves 1206, 1208, 1210 as well as curves 1212, 1214, 1216 show that moisture is detected at the proximal side of the first adhesive layer by the fourth electrode pair, the fourth and fifth electrode, and the fifth electrode pair at a time starting at 60 h until 90 h. As the three electrode pairs are triggered as shown by the decreases shown by 1206, 1208, 1210 and as the curves 1212, 1214, 1216 show a gradient below 80%, this is indicative of the presence of sweat at the proximal side of the first adhesive layer.

At a time of 30 min, curve 1202 shows that moisture is detected by the first electrode pair as the first parameter data crosses the upper voltage threshold value while curve 1204 shows that moisture is not detected by the second electrode pair as the second parameter data has not crossed the upper voltage threshold value. At this stage, it is determined that the ostomy appliance is in a first operating state.

At time around 40 h, curve 1204 shows that moisture is detected by the second electrode pair as the second parameter data crosses the upper voltage threshold value. At this stage, it is determined that the ostomy appliance is in a second operating state.

Figure 16:
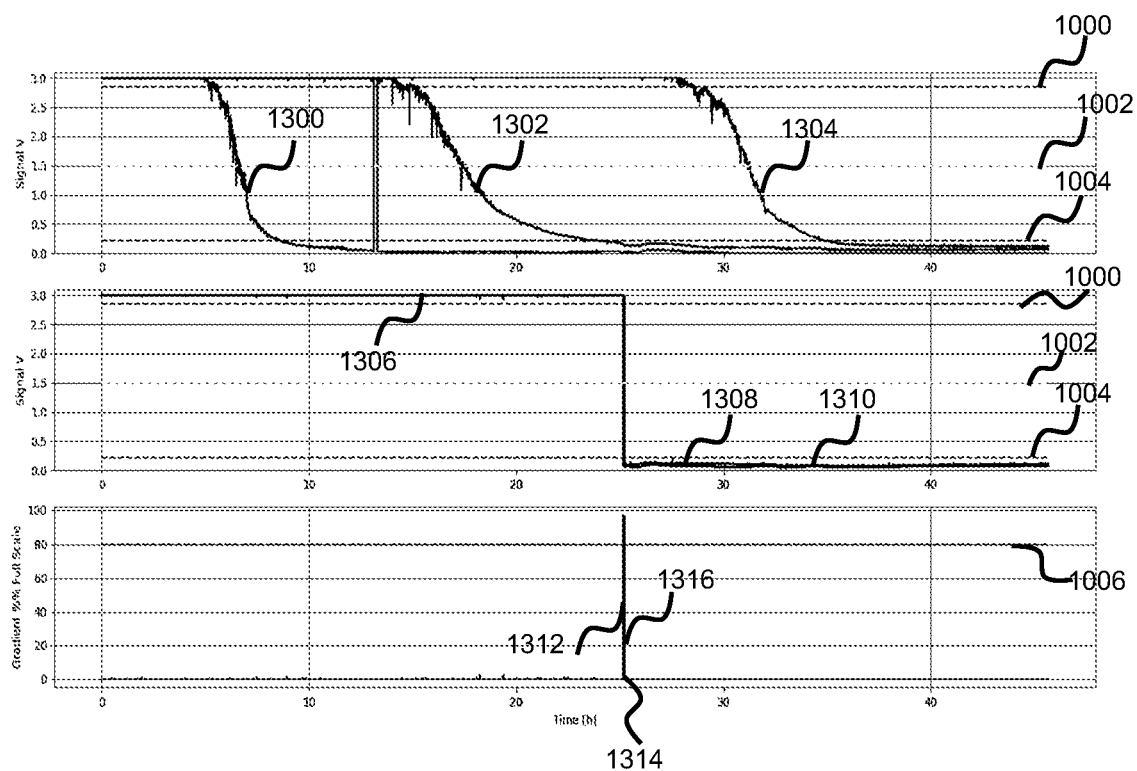
FIG. 16 is an exemplary graphical representation of parameter data as a function of time.

FIG. 16 shows an exemplary graphical representation of parameter data as a function of time. In this example, the parameter data in the y-axis is in Volts and time is in the x-axis. Curve 1300 shows, as a function of time, first parameter data indicative of voltage measured by the first electrode pair of the base plate. Curve 1302 shows, as a function of time, second parameter data indicative of voltage measured by the second electrode pair of the base plate. Curve 1304 shows, as a function of time, third parameter data indicative of voltage measured by the third electrode pair of the base plate. Curves 1306, 1308, 1310 show, as a function of time, fourth primary parameter indicative of voltage measured by the fourth electrode pair of the base plate, fourth secondary parameter indicative of voltage measured by the fourth electrode and the fifth electrode of the base plate, and fourth tertiary parameter indicative of voltage measured by the fifth electrode pair of the base plate respectively. Curves 1312, 1314, 1316 show, as a function of time, a gradient of fourth primary parameter indicative of voltage gradient measured by the fourth electrode pair of the base plate, a gradient of fourth secondary parameter indicative of voltage gradient measured by the fourth electrode and the fifth electrode of the base plate, and a gradient of fourth tertiary parameter indicative of voltage gradient measured by the fifth electrode pair of the base plate respectively. FIG. 16 shows the upper voltage threshold value represented as curve 1000, the medium voltage threshold value represented as curve 1002, the lower voltage threshold value represented as curve 1004, and curve 1006 is a gradient limit.

Curves 1306, 1308, 1310 as well as curves 1312, 1314, 1316 show that moisture is detected at the proximal side of the first adhesive layer by the fourth electrode pair at a time starting at around 25 h. As leakage electrodes (i.e. the fourth electrode pair, the fourth and fifth electrode, and the fifth electrode pair) are trigger as shown by the decreases shown by 1306, 1308, 1310 and as curve 1312, 1314, 1316 show a gradient above 80%, this is indicative of the presence of output at the proximal side of the first adhesive layer. This indicate severe leakage. It may be determined that the ostomy appliance is in a sixth operating state.

At a time of 5*h*, curve 1300 shows that moisture is detected by the first electrode pair as the first parameter data crosses the upper voltage threshold value while curve 1302 shows that moisture is not detected by the second electrode pair as the second parameter data has not crossed the upper voltage threshold value. At this stage, it is determined that the ostomy appliance is in a first operating state.

At time around 15 h, curve 1302 shows that moisture is detected by the second electrode pair as the second parameter data crosses the upper voltage threshold value. At this stage, it is determined that the ostomy appliance is in a second operating state.

At time around 30 h, curve 1304 shows that moisture is detected by the third electrode pair as the third parameter data crosses the upper voltage threshold value. In an example where the curves 1306, 1308, 1310 had not dropped below corresponding thresholds, curve 1304 indicates that moisture has reached the third electrode pair, and the present disclosure enables determining that the ostomy appliance is in a third operating state.

Figure 17:
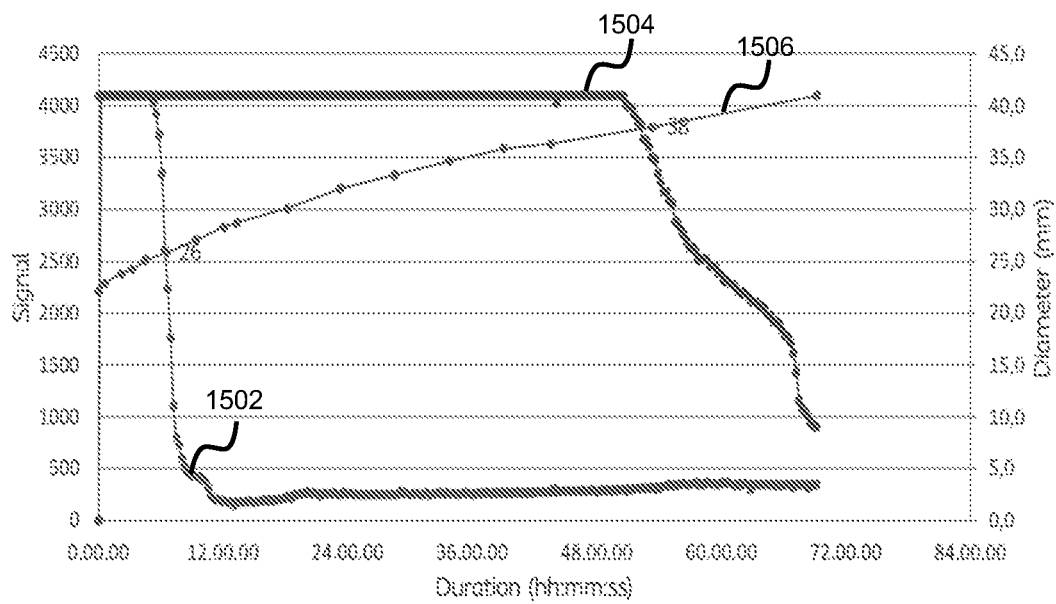
FIG. 17 is an exemplary graphical representation of parameter data as a function of time and a whitening zone diameter as a function of time.

FIG. 17 shows an exemplary graphical representation of parameter data as a function of time and a whitening zone diameter (e.g. related to a radial thickness of a whitening ring surrounding the stomal opening) as a function of time. FIG. 17 illustrates the moisture propagation in the first adhesive layer as a function of time, and illustrates a correlation between parameter data detected by the first electrode pair and the second electrode pair of the base plate and actual moisture on the proximal surface of the first adhesive layer of the base plate. The actual moisture propagation in the first adhesive layer may appear as a whitening zone (e.g. a white ring around the stomal opening) in the first adhesive layer. Moisture affects the first adhesive layer in that the moisture reacts with the composition of the first adhesive layer to form the white ring around the stomal opening, and thereby reduces adhesive performance of the base plate. FIG. 17 is obtained by experiments where water is applied from the stomal opening of the base plate to follow, using the electrodes of the base plate, the radial propagation of moisture leading to radial erosion of the first adhesive layer of the base plate.

Curve 1502 shows, as a function of time, first parameter data indicative of voltage measured by the first electrode pair of the base plate. Curve 1504 shows, as a function of time, second parameter data indicative of voltage measured by the second electrode pair of the base plate. Curve 1506 shows a diameter of the white ring as a function of time. The first parameter data shows a decrease in e.g. voltage measured by the first electrode pair over time. It is also seen that the voltage of the second electrode pair drops at a later time than when the first parameter data shows a decrease in e.g. voltage dropped. This correlates well with the diameter of the white ring which goes from around 25-26 mm when the first electrode pair is triggered (e.g. first parameter data shows a decrease) to 38 mm when the second electrode pair is triggered (second parameter data shows a decrease). This corresponds substantially to the location of the first electrode pair at twice the first radial distance R1, and of the second electrode pair at twice the second radial distance R2.

It is noted that various regions and countries have various routines and recommendations to support optimal use of an ostomy appliance. For example, in regions of Europe, it may be indicated to the user that an ostomy appliance with a base plate as disclosed herein is an optimal state (corresponding to a first operating state) when the radial thickness of the whitening ring is between 0-15 mm (for a user not in compliance with a preferred use), such as between 0-7 mm (for a user in compliance with a preferred use), such as between 0-5 mm (recommended by a nurse).

For example, in Europe, it may be indicated to the user that an ostomy appliance with a base plate as disclosed herein is in suboptimal state (corresponding to a second operating state) and thereby indicate a consideration to change the base plate when the radial thickness of the whitening ring is such as between 5-10 mm (recommended by a nurse), between 7 mm and 10 mm (for a user in compliance with a preferred use), and/or between 15 mm and 30 mm (for a user not in compliance with a preferred use).

For example, in Europe, it may be indicated to the user that an ostomy appliance with a base plate as disclosed herein is in a poor state (corresponding to a third operating state) and indicate a request to change the base plate when the radial thickness of the whitening ring is more than 10 mm (recommended by a nurse), such as more than 15 mm (for a user in compliance with a preferred use), such as more than 30 mm (for a user not in compliance with a preferred use).

For example, in other regions (e.g. America), it may be indicated to the user that an ostomy appliance with a base plate as disclosed herein is an optimal state (corresponding to a first operating state) when the radial thickness of the whitening ring is between 0-20 mm (for a user not in compliance with a preferred use), such as between 0-10 mm (for a user in compliance with a preferred use), such as between 0-10 mm (recommended by a nurse).

For example, in other regions (e.g. America), it may be indicated to the user that an ostomy appliance with a base plate as disclosed herein is in suboptimal state (corresponding to a second operating state) and thereby indicate a consideration to change the base plate when the radial thickness of the whitening ring is such as between 10 mm and 20 mm (recommended by a nurse), between 10 mm and 20 (for a user in compliance with a preferred use), and/or between 20 mm and 40 mm (for a user not in compliance with a preferred use).

For example, in other regions (e.g. America), it may be indicated to the user that an ostomy appliance with a base plate as disclosed herein is in a poor state (corresponding to a third operating state) and indicate a request to change the base plate when the radial thickness of the whitening ring is more than 20 mm (recommended by a nurse), such as more than 20 mm (for a user in compliance with a preferred use), such as more than 40 mm (for a user not in compliance with a preferred use).

The disclosed methods, and accessory devices allow to accommodate the regional preferences of user in their use of the ostomy appliance so as to adjust thresholds for the operating states to the regional preference or use.

Figure 18A:
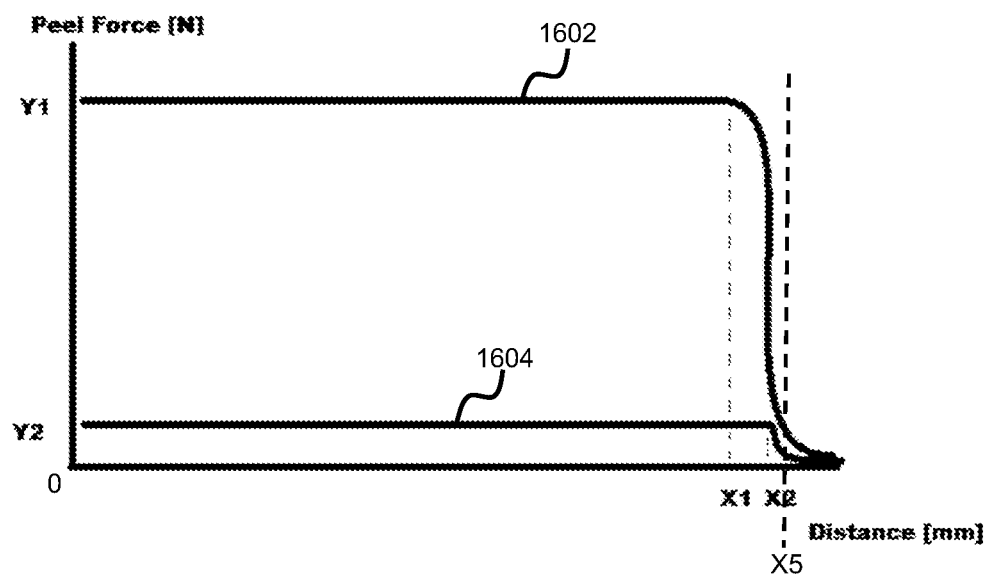
FIGS. 18A-18B are exemplary graphical representations of peel force as a function of a peeling distance travelled by a peeling action exercising the peel force on a first adhesive layer of a base plate.
Figure 18B:
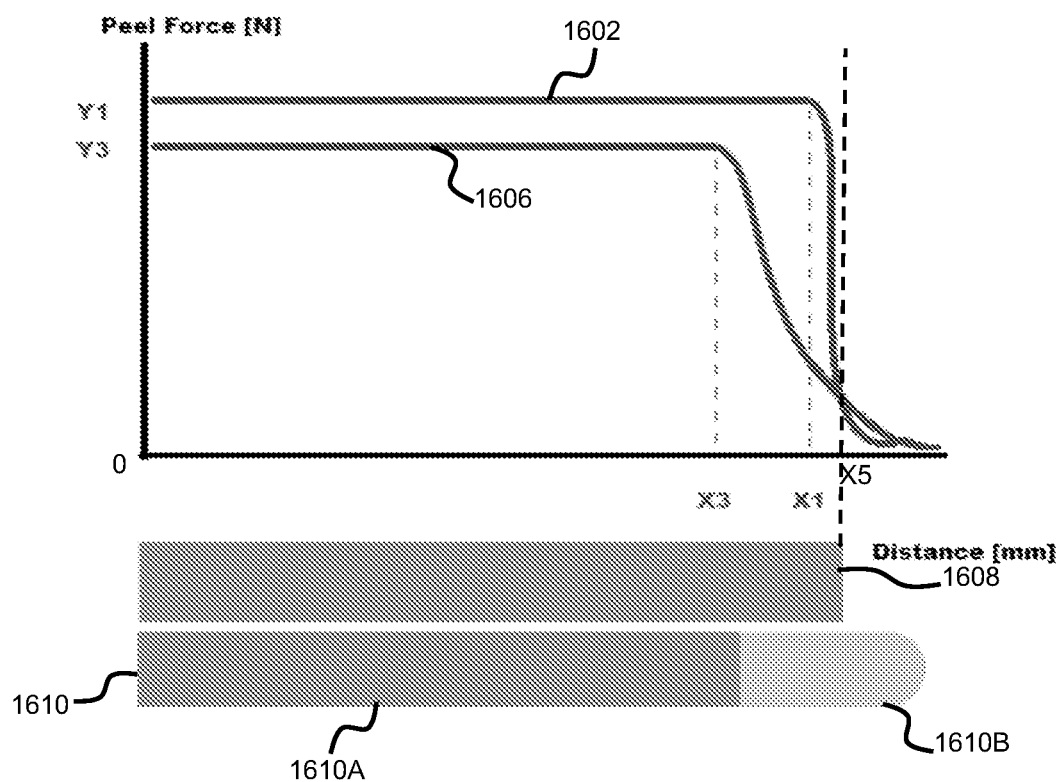

FIGS. 18A-18B shows exemplary graphical representations of peel force as a function of a peeling distance travelled by a peeling action exercising the peel force (e.g. perpendicularly to the proximal (or distal) surface of the first adhesive layer) on a first adhesive layer of a base plate disclosed herein. The peel force relates to a required force to peel the first adhesive layer off the skin surface. The peeling distance is with respect to one end of the first adhesive layer where the peel force starts to be exercised. The peeling distance relates to the size or length of the first adhesive layer and thereby may relate to a size or length of a portion the first adhesive layer affected by moisture and of a portion of the first adhesive layer not affected by moisture. The peel forces illustrated in FIGS. 18A-18B are representative of adhesive performance of the first adhesive layer of the base plate to the skin surface.

Composition of the first adhesive layer of the base plate as disclosed herein in one or more embodiments is formulated to provide adhesion of the base plate to the skin surface of the user when the base plate is worn and to maintain a dry and healthy skin surface. Avoiding maceration of skin when occluding the skin with an adhesive is done by transporting sweat away from the skin and into the first adhesive layer by means of e.g. hydrocolloid types and adhesive (e.g. hydrocolloid adhesives) forming part of an absorbing element of the first adhesive layer.

For example, when the absorbing element is in contact with moisture, (e.g. water, sweat, urine or faeces), the absorbing element absorb the moisture. This reduces the adhesion of the first adhesive layer to the skin.

For example, the first adhesive layer goes from a dry adhesive state with acceptable adhesive performance (e.g. acceptable adhesion and cohesion) in to a wet adhesive state (e.g. reduced or non-adhesion and low cohesion gel).

Curve 1602 of FIGS. 18A and 18B shows a peel force applied to the first adhesive layer as a function of a peeling distance travelled by a peeling action exercising the peel force on the first adhesive layer in a dry adhesive state, (e.g. not affected by moisture). The peel force is expressed in Newtons while the peeling distance is expressed in mm. The length of the first adhesive layer in dry adhesive state is illustrated by X5, corresponding to length of the first adhesive layer 1608 in dry adhesive state.

Curve 1602 shows that the peel force applied to the first adhesive layer in a dry adhesive state is equal to Y1 when the peeling distance is less than X1. At X1, the peeling force drops as the peeling distance increases towards X5 and the end of the first adhesive layer.

Curve 1604 of FIG. 18A shows a peel force applied to the first adhesive layer as a function of a peeling distance travelled by a peeling action exercising the peel force on the first adhesive layer in a wet adhesive state, (e.g. affected by moisture to the point of reaching a completely wet adhesive state, where the first adhesive layer has become a gel).

Curve 1604 shows that when the peeling distance is less than X2, the peel force applied to the first adhesive layer in a wet adhesive state is equal to Y2 which has much lower value than Y1. This shows that the adhesive performance of the first adhesive layer is reduced when the first adhesive layer is in a wet adhesive state. At X2, the peeling force drops as the peeling distance increases until the end of the first adhesive layer. It is noted that X2 is larger than X1, because the first adhesive layer in a wet adhesive state extends in volume, and thus in length due to the gelling of the components of the first adhesive layer.

The peel experiment illustrated in FIG. 18A shows a loss of adhesive performance when the first adhesive is in a wet adhesive state.

Curve 1606 of FIG. 18B shows a peel force applied to the first adhesive layer as a function of a peeling distance travelled by a peeling action exercising the peel force on the first adhesive layer illustrated 1610 which comprises a first portion 1610A in a dry adhesive state and a second portion 1610B in a wet adhesive state, (e.g. affected by moisture to the point of reaching a completely wet adhesive state, where the first adhesive layer has become a gel).

Curve 1606 shows that when the peeling distance is less than X3, the peel force applied to the first adhesive layer in a wet adhesive state is equal to Y3 which has lower value than Y1. This shows that the adhesive performance of the first adhesive layer is reduced when the first adhesive layer comprises a portion in a wet adhesive state. At X3, the peeling force drops as the peeling distance increases until the end of the first adhesive layer. It is noted that X3 corresponds to the length of the portion 1610A in dry adhesive state.

The peel experiment illustrated in FIG. 18B shows a loss of adhesive performance when the first adhesive is partly in a wet adhesive state.

Accordingly, FIGS. 18A-18B demonstrate that the operating state determined based on monitor data is indicative of adhesive performance of the base plate.

Figure 19A:
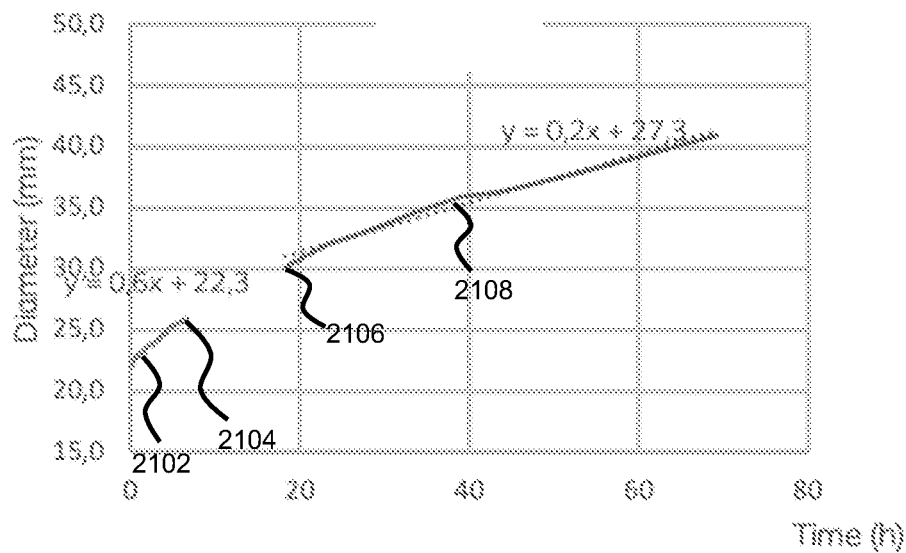
FIGS. 19A-19B are exemplary graphical representations of a whitening zone diameter.
Figure 19B:
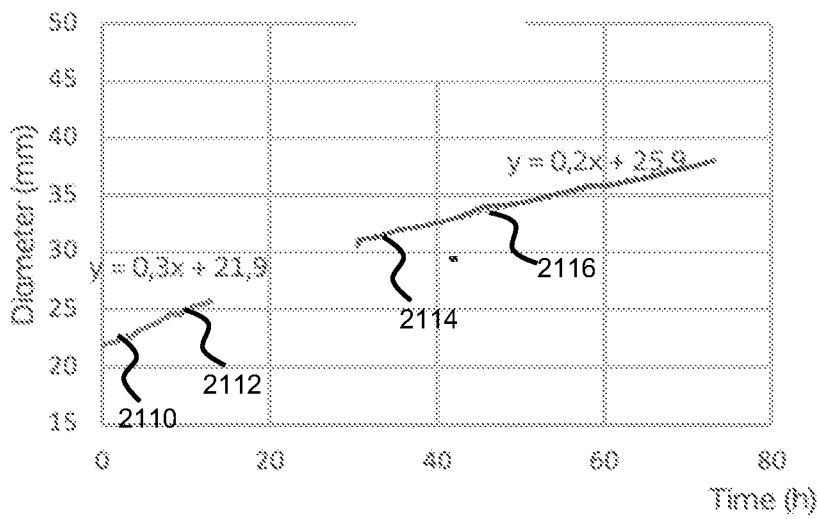

FIGS. 19A-19B show exemplary graphical representations of a whitening zone diameter (e.g. related to a radial thickness of a whitening ring surrounding the stomal opening) as a function of time. FIGS. 19A-19B illustrates the moisture propagation in the first adhesive layer as a function of time, and illustrates a diametral velocity of the moisture propagation on the proximal surface of the first adhesive layer of the base plate. The actual moisture propagation in the first adhesive layer may appear as a whitening zone (e.g. a white ring around the stomal opening) in the first adhesive layer. FIGS. 19A-19B show measurements of a diameter of the whitening zone as a function of time as moisture propagates. Moisture affects the first adhesive layer in that the moisture reacts with the composition of the first adhesive layer to form the white ring around the stomal opening, and thereby reduces adhesive performance of the base plate.

FIG. 19A is obtained by experiments where water is applied from the stomal opening of the base plate of a first type to measure a velocity of the radial propagation of moisture leading to radial erosion of the first adhesive layer of the base plate of the first type.

FIG. 19B is obtained by experiments where water is applied from the stomal opening of the base plate of a second type to measure a velocity the radial propagation of moisture leading to radial erosion of the first adhesive layer of the base plate of the second type. The second type is different from the first type, in that the composition of the first adhesive layer may be different than the first adhesive layer of the second type when compared to the first type.

Curve 2104 shows, as a function of time, a diameter of the white ring of a base plate of the first type measured from a cut for a stomal opening to the first electrode pair.

Curve 2102 shows a linear approximation of curve 2104, and thereby characterizes the velocity from the cut to the first electrode pair. The linear approximation may be formulated as a linear equation of the type $Y=v01*X+A$, where Y is the diameter of the white ring in millimetres (mm), X is time in hours, v01 is a diametral velocity of propagation of moisture in the base plate of the first type from the cut to the first electrode pair, and A relates to the diameter of the cut. In the experiment illustrated in FIG. 19A, v01=0.6 mm/h and A is 22 (i.e. the cut for the stomal opening has a diameter of 22 mm). Other experiments have shown that v01 may be in the range of 0.5 mm/h to 0.8 mm/h, with an average diametral velocity v01 of 0.65 mm/h for moisture to propagate from the cut to the first electrode pair. To obtain radial velocity V01 for moisture to propagate from the cut to the first electrode pair from the results of FIG. 19A, the diametral velocity v01 is to be divided by two: V01=0.3 mm/h for the illustrated experiment.

Curve 2106 shows, as a function of time, a diameter of the white ring of a base plate of the first type measured from the first electrode pair to the second electrode pair.

Curve 2108 shows a linear approximation of curve 2106, and thereby characterizes the velocity from the first electrode pair to the second electrode pair. The linear approximation may be formulated as a linear equation of the type $Y=v12*X+B$, where Y is the diameter of the white ring in millimetres (mm), X is time in hours, v12 is a diametral velocity of propagation of moisture in the base plate of the first type from the first electrode pair to the second electrode pair, and B relates to approximate location of the first electrode pair from the center of the stomal opening. In the experiment illustrated in FIG. 19A, v12=0.2 mm/h and B is 27.3 mm (i.e. the first electrode pair is place around 27.3 mm). Other experiments have shown that v12 may be in the range of 0.15 mm/h to 0.22 mm/h, with an average diametral velocity of 0.18 mm/h for moisture to propagate from the first electrode pair to the second electrode pair. To obtain radial velocity V12 for moisture to propagate from the first electrode pair to the second electrode pair from the results of FIG. 19A, the diametral velocity v12 is to be divided by two: V12=0.1 mm/h for the illustrated experiment.

Curve 2112 shows, as a function of time, a diameter of the white ring of a base plate of the second type measured from a cut for a stomal opening to the first electrode pair.

Curve 2110 shows a linear approximation of curve 2112, and thereby characterizes the velocity from the cut to the first electrode pair. The linear approximation may be formulated as a linear equation of the type $Y=v01*X+A$, where Y is the diameter of the white ring in millimetres (mm), X is time in hours, v01 is a diametral velocity of propagation of moisture in the base plate of the second type from the cut to the first electrode pair, and A relates to the diameter of the cut. In the experiment illustrated in FIG. 19B, v01=0.3 mm/h and A is 21.9 (i.e. the cut for the stomal opening has a diameter of 21.9 mm). Other experiments have shown that v01 may be in the range of 0.2 mm/h to 0.32 mm/h, with an average diametral velocity v01 of 0.275 mm/h for moisture to propagate from the cut to the first electrode pair. To obtain radial velocity V01 for moisture to propagate from the cut to the first electrode pair from the results of FIG. 19B, the diametral velocity v01 is to be divided by two: V01=0.15 mm/h for the illustrated experiment.

Curve 2114 shows, as a function of time, a diameter of the white ring of a base plate of the second type measured from the first electrode pair to the second electrode pair.

Curve 2116 shows a linear approximation of curve 2114, and thereby characterizes the velocity from the first electrode pair to the second electrode pair. The linear approximation may be formulated as a linear equation of the type $Y=v12*X+B$, where Y is the diameter of the white ring in millimetres (mm), X is time in hours, v12 is a diametral velocity of propagation of moisture in the base plate of the second type from the first electrode pair to the second electrode pair, and B relates to approximate location of the first electrode pair from the center of the stomal opening. In the experiment illustrated in FIG. 19B, v12=0.2 mm/h and B is 25.9 mm (i.e. the first electrode pair is place around 25.9 mm). Other experiments have shown that v12 may be in the range of 0.15 mm/h to 0.22 mm/h, with an average diametral velocity of 0.1 mm/h for moisture to propagate from the first electrode pair to the second electrode pair. To obtain radial velocity V12 for moisture to propagate from the first electrode pair to the second electrode pair from the results of FIG. 19B, the diametral velocity v12 is to be divided by two: V12=0.5 mm/h for the illustrated experiment.

The experiments illustrated in FIGS. 19A-19B correspond substantially with the location of the first electrode pair at twice the first radial distance R1, and of the second electrode pair at twice the second radial distance R2.

The present disclosure exploits the derivable velocities to determine a future operating state based on monitor data and/or current operating state and/or previous operating states to adjust notifications of an ostomy appliance.

Figure 20A:
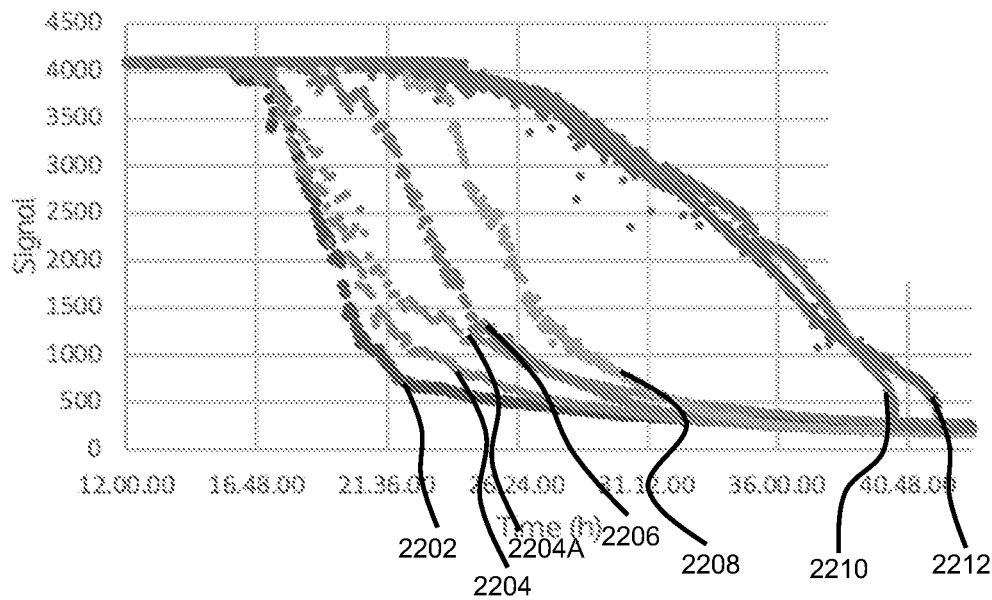
FIG. 20A is an exemplary graphical representation of first parameter data as a function of time for various semi-solid matter scenarios.

FIG. 20A show an exemplary graphical representation of first parameter data as a function of time. In this example, the parameter data in the y-axis is in millivolts and time is in the x-axis.

FIG. 20A is obtained by experiments where semi-solid matter with various degrees of dilution is applied from the stomal opening of the base plate to follow, using the first electrode pair of the base plate, the radial propagation of moisture leading to radial erosion of the first adhesive layer of the base plate. Dilution is performed with tap water and semi-solid matter.

The exemplary results of FIG. 20A illustrates and mimics how the moisture content of the output would affect the first parameter data and thereby the operating state. This is done by mixing a semi-solid matter with water to various dilution factors. The content of moisture in real life changes the viscosity of the output and is affected by one or more factors: nutrition (type of food eaten by user, water intake, etc.), medication (e.g. vitamins/supplements, prescriptions, etc.), and health data (e.g. medical conditions of the user, diseases, ostomist, ileostomist, etc.).

Curve 2202 shows, as a function of time, first parameter data indicative of voltage measured by the first electrode pair of the base plate when a mixture of 0% semi-solid matter and 100% tap water is applied from the stomal opening of the base plate.

Curve 2204 shows, as a function of time, first parameter data indicative of voltage measured by the first electrode pair of the base plate when a mixture of 30% semi-solid matter and 70% tap water is applied. Curve 2204A shows, as a function of time, first parameter data indicative of voltage measured by the first electrode pair of the base plate when a mixture of 30% semi-solid matter and 70% tap water is applied.

Curve 2206 shows, as a function of time, first parameter data indicative of voltage measured by the first electrode pair of the base plate when a mixture of 30% semi-solid matter and 70% tap water is applied.

Curve 2208 shows, as a function of time, first parameter data indicative of voltage measured by the first electrode pair of the base plate when a mixture of 50% semi-solid matter and 50% tap water is applied.

Curve 2210 shows, as a function of time, first parameter data indicative of voltage measured by the first electrode pair of the base plate when a mixture of 100% semi-solid matter and 0% tap water is applied.

Curve 2212 shows, as a function of time, first parameter data indicative of voltage measured by the first electrode pair of the base plate when a mixture of 100% semi-solid matter and 0% tap water is applied.

It may be noted that the more diluted the output is the earlier the first electrode pair is triggered.

Figure 20B:
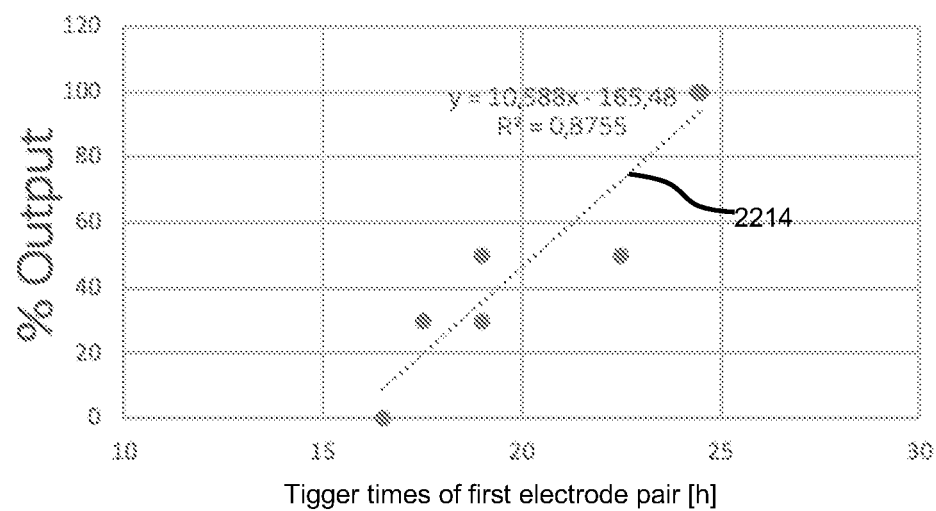
FIG. 20B is an exemplary graphical representations of first parameter data as a function of percentage of semi-solid matter in the mixture applied to the stomal opening.

FIG. 20B shows exemplary graphical representations of first parameter data as a function of percentage of output in the mixture applied.

Curve 2214 shows a linear approximation relating the trigger times of the first electrode pair to the percentage of semi-solid matter, and thereby characterizes how the viscosity of the semi-solid matter affects the propagation of moisture in the first adhesive layer. The curve 2214 represents a linear equation with a coefficient of 10.6 with an approximation precision of 87% for the exemplary results. This support a determination of a future operating state based one or more of: nutritional data (type of food eaten by user, water intake, etc.), medication intake data (e.g. vitamins/supplements, prescriptions, etc.), and health data (e.g. medical conditions of the user, diseases, ostomist, ileostomist, etc.).

It may be envisaged that a thin output may be detected based the early triggering time of the first electrode pair and thereby the future operating state may be determined accordingly.

Due to activity (e.g. sports, bending, movement), experimental results have shown that the operating state may be affected negatively by a reducing factor ranging from 2 to 10 compared to when the user has no or little activity (e.g. a sedentary user), For example, a wear time may be reduced by a scaling factor of 2 to 10 due to an extensive activity.

Figure 21A:
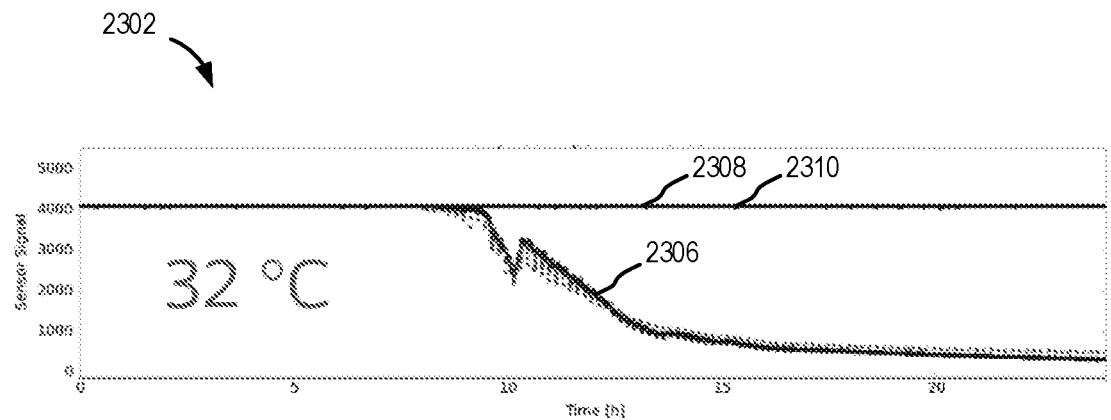
FIGS. 21A-21B are exemplary graphical representations of parameter data as functions of time for different predetermined temperatures.
Figure 21B:
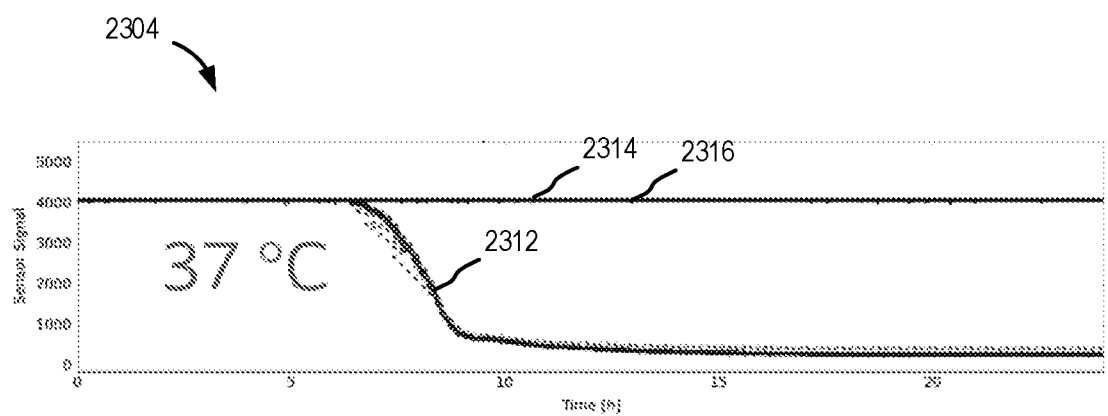

FIG. 21A shows an exemplary graphical representation 2302 of parameter data as a function of time for a first type of base plate at a first predetermined temperature. The first predetermined temperature in the example depicted in FIG. 21A is 32 degrees Celsius. FIG. 21B shows an exemplary graphical representation 2304 of parameter data as a function of time for the first type of base plate at a second predetermined temperature. The second predetermined temperature in the example depicted in FIG. 21B is 37 degrees Celsius. The temperatures were selected to closely approximate human skin temperature.

FIGS. 21A and 21B were obtained by applying fluid at a stomal opening of a base plate, wherein the stomal opening had a diameter of 22 mm. The residual humidity of the environment for both experiments was 50%. As the fluid was absorbed by the base plate over time and the fluid propagated radially from the stomal opening outward, parameter data (e.g. voltages (mV)) was measured between a first electrode pair, a second electrode pair, and/or a third electrode pair respectively.

Specifically, in FIG. 21A, curve 2306 shows, as a function of time, a decrease in voltage for the first electrode pair at approximately 8.3 hours. Curve 2308 shows, as a function of time, a constant voltage for the second electrode pair. And, curve 2310 shows, as a function of time, a constant voltage for the third electrode pair.

By comparison, in FIG. 21B, curve 2312 shows a decrease in voltage for the first electrode pair at approximately 7.6 hours. Curve, 2314 shows, as a function of time, a constant voltage for the second electrode pair. And, curve 2316 shows, as a function of time, a constant voltage for the third electrode pair.

Stated another way, in this example, moisture propagated approximately 11% faster when the temperature was 37 degrees Celsius in comparison to when the temperature was 32 degrees Celsius. This comparison shows that as temperature increases, wear time of the base plate decreases due to faster moisture propagation and adhesion degradation.

Another experiment was conducted where the propagation speed of fluid, applied at the stomal opening of a second type of base plate, was measured. Similar to the experiment depicted in FIGS. 21A, 21B, the stomal opening had a diameter of 22 mm and the residual humidity of the environment was 50%. The second type of base plate is different than the first type of base plate, in that the composition of the first adhesive layer of the first type of base plate is different than the composition of the first adhesive layer of the second type of base plate.

In this experiment, the fluid propagated between center of the hole and first electrode pair at approximately 0.15 mm/hour when the temperature was 32 degrees Celsius. In comparison, the fluid propagated at approximately 0.2 mm/hour when the temperature was 37 degrees Celsius. As such, this experiment similarly found that for another type of base plate as temperature increases, wear time of the second type of base plate decreases due to faster moisture propagation and adhesion degradation.

In view of the above results, a scaling factor may be applied to the operating state (e.g. wear time) of a base plate such that the scaling factor affects negatively the operating state (e.g. decreases the wear time) of the base plate as temperature increases and/or the scaling factor affects positively the operating state (e.g. increases the wear time) of the base plate as temperature decreases.

In some embodiments, the scaling factor may be predetermined. In these embodiments, the predetermined scaling factor may be constant. Alternatively, the predetermined scaling factor may be iteratively adjusted based on when the first electrode pair, the second electrode pair, and/or the third electrode pair are triggered. In at least some of these embodiments, the predetermined scaling factor may be iteratively adjusted.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES 1 ostomy system
2 ostomy appliance
4 base plate
6 monitor device
8 accessory device
10 server device
12 network
14 coupling member
16 coupling ring
18, 18A, 18B, 18C, 18D stomal opening
20 docking station
22 first connector
24 user interface
100 monitor device housing
101 processor
102 first interface
104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part
121 power unit
122 antenna
124 wireless transceiver
126 loudspeaker
128 haptic feedback element
140 sensor unit
142 sensor data
144 first sensor
146 second sensor
200 first adhesive layer
200A distal surface of first adhesive layer
200B proximal surface of first adhesive layer
202 second adhesive layer
202A distal surface of second adhesive layer
202B proximal surface of second adhesive layer
204 electrode assembly
204A distal surface of electrode assembly
204B proximal surface of electrode assembly
206 release liner
206A distal surface of the release liner
206B proximal surface of the release liner
208 top layer
208A distal surface of the top layer
208B proximal surface of the top layer
209 coupling ring
210 coupling part of first connector
211 first connector
212 terminals of first connector
213 first intermediate element
213A distal surface of first intermediate element
213B proximal surface of first intermediate element
214 support layer of electrode assembly
214A distal surface of support layer
214B proximal surface of support layer
216 electrodes of electrode assembly
217 connection parts of electrodes
218, 219 masking element
218A distal surface of masking element
218B proximal surface of masking element
220, 220A, 220B electrode configuration
222 ground electrode
222A ground connection part
222B ground sensing part
222C ground connector part
224 first electrode
224A first connection part 224B first sensing part
224C first conductor part
226 second electrode
226A second connection part
226B second sensing part
226C second conductor part
228 third electrode
228A third connection part
228B third sensing part
228C third conductor part
230 fourth electrode
230A fourth connection part
230B fourth sensing part
232 fifth electrode
232A fifth connection part
232B fifth sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
252 fifth terminal opening
254 primary sensor point openings of masking element
254A primary first sensor point opening
254B primary second sensor point opening
256 secondary sensor point openings of masking element
256A secondary first sensor point opening
256B secondary second sensor point opening
258 tertiary sensor point openings of masking element
258A tertiary first sensor point opening
258B tertiary second sensor point opening
260 primary sensor point openings of first adhesive layer
260A primary first sensor point opening
260B primary second sensor point opening
262 secondary sensor point openings of first adhesive layer
262A secondary first sensor point opening
262B secondary second sensor point opening
264 tertiary sensor point openings of first adhesive layer
264A tertiary first sensor point opening
264B tertiary second sensor point opening
282 ground terminal element
282A ground terminal
284 first terminal element
284A first terminal
286 second terminal element
286A second terminal
288 third terminal element
288A third terminal
290 fourth terminal element
290A fourth terminal
292 fifth terminal element
292A fifth terminal
300 method for configuring notification settings of an ostomy user application
302 displaying, on the display, a notification settings user interface comprising one or more control objects including a first control object
304 while displaying the notification settings user interface, detecting 304, e.g. by contact, a first input directed to the first control object
306 adjusting, based on the detected first input, a first notification setting parameter that corresponds to the first control object
306a adjusting, based on the characteristic feature of the detected first input, a first notification setting parameter
308 displaying an updated first control object in the notification settings user interface.
310 generating, based on the adjusted notification setting, one or more notifications including a first notification
310a obtaining monitor data from the one or more devices, obtaining 310b context data
310b obtaining context data
310c determining one or more operating states of the ostomy appliance based on the monitor data and the context data
310d generating the one or more notifications based on the adjusted first notification setting parameter and the one or more operating states
310e determining whether at least one of the one or more operating states meets one or more notification criteria
310f generating the one or more notifications including the first notification based on the adjusted notification setting;
310g displaying the first notification on the display
310h generating the one or more notifications based on the adjusted first notification setting parameter and the calendar data
310i generating the one or more notifications based on the adjusted first notification setting parameter and location data
A to support transition from FIGS. 11a to 11b
312 detecting an authentication input to unlock the device; in accordance with successful verification of the authentication input;
314 in response to detecting the authentication input to unlock the device, verifying the authentication input;
316 unlocking the accessory device
318 in response to unlocking of the accessory device, in accordance with successful verification of the authentication input, displaying a first user interface including the first notification (e.g. overlaid on the first user interface).
320 detecting a biometric input;
322 in response to detecting the biometric input, verifying the biometric input;
324 in accordance with successful verification of the biometric input, displaying the one or more notifications including the first notification comprises displaying a long version of the first notification
326 in accordance with unsuccessful verification of the biometric input, displaying the one or more notifications including the first notification comprises displaying a short version of the first notification
328 detecting a second input selecting the first notification.
330 in response to detecting the second input, opening the ostomy user application
332 displaying a second user interface comprising a third user interface object representing the current operating state of the ostomy appliance and a fourth user interface object representing the one or more future operating states of the ostomy appliance
401 memory of accessory device
402 processor of accessory device
403 interface of accessory device
403a display of accessory device
500 exemplary first user interface 502 first primary user interface object representing a first notification
504 additional user interface object representing an earlier notification
506 additional user interface object representing earlier notification
520 exemplary second user interface
522 third user interface object representing the current operating state of the ostomy appliance
524 fourth user interface object representing the one or more future operating states
526 user interface object representative of a graph
528 user interface object(s) representative of one or more previous operating states
530 user interface object representing a summary status of the base plate
532 wear time user interface object
534 recommendation user interface object
536 user interface object to access notification settings user interface of the user ostomy application
538 fifth user interface object
540 sixth user interface object
600 notification settings user interface
610 first control object for adjusting a first notification setting parameter
610a updated first control object
612 scale for first notification setting parameter
614 the first input resulting in a movement of the first control object 610
620 second control object for adjusting a second notification setting parameter
622 scale for a second notification setting parameter
1000 curve representing the upper voltage threshold value
1002 curve representing the medium voltage threshold value
1004 curve representing the lower voltage threshold value
1006 curve representing a gradient limit
1100 curve showing, as a function of time, first parameter data indicative of voltage measured by the first electrode pair of the base plate
1102 curve showing, as a function of time, second parameter data indicative of voltage measured by the second electrode pair of the base plate
1104 curve showing, as a function of time, third parameter data indicative of voltage measured by the third electrode pair of the base plate
1108 curve showing, as a function of time, fourth primary parameter indicative of voltage measured by the fourth electrode pair of the base plate
1110 curve showing, as a function of time, a gradient of fourth primary parameter indicative of voltage gradient
1112 curve showing, as a function of time, a gradient of fourth secondary parameter indicative of voltage gradient measured
1114 curve showing, as a function of time, a gradient of fourth tertiary parameter indicative of voltage gradient measured
1116 curve showing, as a function of time, a fourth secondary parameter indicative of voltage measured
1118 curve showing, as a function of time, a fourth tertiary parameter indicative of voltage measured
1200 curve showing, as a function of time, third parameter data indicative of voltage measured by the third electrode pair of the base plate
1202 curve showing, as a function of time, first parameter data indicative of voltage measured by the first electrode pair of the base plate
1204 curve showing, as a function of time, second parameter data indicative of voltage measured by the second electrode pair of the base plate
1206 curve showing, as a function of time, a fourth primary parameter indicative of voltage measured by the fourth electrode pair of the base plate
1208 curve showing, as a function of time, a fourth secondary parameter indicative of voltage measured
1210 curve showing, as a function of time, a fourth tertiary parameter indicative of voltage measured
1212 curve showing, as a function of time, a gradient of fourth primary parameter indicative of voltage gradient measured by the fourth electrode pair of the base plate
1214 curve showing, as a function of time, a gradient of fourth secondary parameter data indicative of voltage gradient measured
1216 curve showing, as a function of time, a gradient of fourth tertiary parameter indicative of voltage gradient measured
1300 curve showing, as a function of time, first parameter data indicative of voltage measured by the first electrode pair of the base plate
1302 curve showing, as a function of time, second parameter data indicative of voltage measured by the second electrode pair of the base plate
1304 curve showing, as a function of time, third parameter data indicative of voltage measured by the third electrode pair of the base plate
1306 curve showing, as a function of time, a fourth primary parameter indicative of voltage measured by the fourth electrode pair of the base plate
1308 curve showing, as a function of time, a fourth secondary parameter indicative of voltage measured
1310 curve showing, as a function of time, a fourth tertiary parameter indicative of voltage measured
1312 curve showing, as a function of time, a gradient of fourth primary parameter indicative of voltage gradient measured by the fourth electrode pair of the base plate
1314 curve showing, as a function of time, a gradient of fourth secondary parameter indicative of voltage gradient measured
1316 curve showing, as a function of time, a gradient of fourth tertiary parameter indicative of voltage gradient measured
1502 curve showing, as a function of time, first parameter data indicative of voltage measured by the first electrode pair of the base plate
1504 curve showing, as a function of time, second parameter data indicative of voltage measured by the second electrode pair of the base plate
1506 curve showing a diameter of the white ring as a function of time
1602 curve showing peel force applied to the first adhesive layer in a dry adhesive state as a function of peeling distance
1604 a peel force applied to the first adhesive layer as a function of a peeling distance travelled by a peeling action exercising the peel force on the first adhesive layer in a wet adhesive state
1606 a peel force applied to the first adhesive layer as a function of a peeling distance travelled by a peeling action exercising the peel force on the first adhesive layer partially wet
1608 length of the first adhesive layer 1608 in dry adhesive state 1610 the first adhesive layer which comprises a first portion in a dry adhesive state and a second portion in a wet adhesive state
1610A a first portion in a dry adhesive state
1610B a second portion in a wet adhesive state
2104 curve showing a function of time, a diameter of the white ring of a base plate of the first type measured from a cut for a stomal opening to the first electrode pair
2102 a linear approximation of curve 2104
2106 curve showing, as function of time, a diameter of the white ring of a base plate of the first type measured from the first electrode pair to the second electrode pair
2108 a linear approximation of curve 2106
2110 a linear approximation of curve 2112
2112 curve showing, as function of time, a diameter of the white ring of a base plate of the second type measured from a cut for a stomal opening to the first electrode pair
2114 curve showing, as a function of time, a diameter of the white ring of a base plate of the second type measured from the first electrode pair to the second electrode pair
2116 a linear approximation of curve 2114
2202 curve showing, as a function of time, first parameter data
2204 curve showing, as a function of time, first parameter data
2204A curve showing, as a function of time, first parameter data indicative of voltage measured by the first electrode pair of the base plate when a mixture of 30% output and 70% tap water is applied
2206 curve showing, as a function of time, first parameter data indicative of voltage measured by the first electrode pair of the base plate when a mixture of 30% output and 70% tap water is applied
2208 curve showing, as a function of time, first parameter data indicative of voltage measured by the first electrode pair of the base plate when a mixture of 50% output and 50% tap water is applied
2210 curve showing, as a function of time, first parameter data indicative of voltage measured by the first electrode pair of the base plate when a mixture of 100% output and 0% tap water is applied
2212 curve showing, as a function of time, first parameter data indicative of voltage measured by the first electrode pair of the base plate when a mixture of 100% output and 0% tap water is applied
2214 curve showing a linear approximation relating the trigger times of the first electrode pair to the percentage of output
2302 a graphical representation of parameter data as a function of time at a first predetermined temperature
2304 a graphical representation of parameter data as a function of time at a second predetermined temperature
2306 curve showing, as a function of time, a decrease in voltage for the first electrode pair at a first predetermined temperature
2308 curve showing, as a function of time, a constant voltage for the second electrode pair at the first predetermined temperature
2310 curve showing, as a function of time, a constant voltage for the third electrode pair at the first predetermined temperature
2312 curve showing, as a function of time, a decrease in voltage for the first electrode pair at a second predetermined temperature
2314 curve showing, as a function of time, a constant voltage for the second electrode pair at the second predetermined temperature
2316 curve showing, as a function of time, a constant voltage for the third electrode pair at the second predetermined temperature

The invention claimed is:

1. A method, performed in an accessory device, wherein the accessory device comprises an interface configured to communicate with one or more devices of a medical system, the interface comprising a display, wherein the medical system comprises a medical appliance configured to be placed on a skin surface of a user, wherein the medical appliance comprises a base plate, the method comprising:
displaying, on the display, a notification settings user interface of medical system user application, the notification settings user interface comprising one or more control objects including a first control object, wherein the notification settings user interface is configured to adjust notification setting parameters of the medical system user application,
while displaying the notification settings user interface, detecting, by contact, a first input directed to the first control object,
in response to detecting the first input:
in accordance with a determination that the first input meets one or more first control criteria:
adjusting, based on the detected first input, a first notification setting parameter that corresponds to the first control object; and
displaying an updated first control object in the notification settings user interface.

2. The method according to claim 1, wherein the first input comprises a touch, and/or a movement of contact.

3. The method according to claim 1, wherein the one or more first control criteria comprise a primary criterion that is met when a characteristic feature of the first input exceeds a threshold during the first input.

4. The method according to claim 1, wherein adjusting, based on the detected first input, a first notification setting parameter comprises adjusting, based on the characteristic feature of the detected first input, a first notification setting parameter.

5. The method according to claim 1, the method comprising generating, based on the adjusted first notification setting parameter, one or more notifications including a first notification.

6. The method according to claim 5, wherein generating, wherein generating, based on the adjusted first notification setting parameter, the one or more notifications comprises:
obtaining monitor data from the one or more devices,
obtaining context data,
determining one or more operating states of the medical appliance based on the monitor data and the context data, wherein an operating state is indicative of future adhesive performance of the medical appliance, and
generating the one or more notifications based on the adjusted first notification setting parameter and the one or more operating states.

7. The method according to claim 6, wherein generating the one or more notifications based on the adjusted first notification setting parameter and the one or more operating states comprises:
determining whether at least one of the one or more operating states meets one or more notification criteria, and in accordance with the determination that at least one of the one or more operating states meets one or more notification criteria:
generating the one or more notifications including the first notification based on the adjusted first notification setting parameter; and
displaying the one or more notifications including the first notification on the display.

8. The method according to claim 5, wherein the one or more operating states comprise at least one of: a wear time, a quality of adhesion, and a moisture pattern representation.

9. The method according to claim 5, wherein obtaining the context data comprises obtaining the context data from a second application different from the medical system user application.

10. The method according to claim 5, wherein obtaining the context data comprises obtaining the context data comprising calendar data from a calendar application installed on the accessory device.

11. The method according to claim 10, wherein generating, based on the adjusted first notification setting parameter, one or more notifications comprises generating the one or more notifications based on the adjusted first notification setting parameter and the calendar data.

12. The method according to claim 5, wherein obtaining the context data comprises obtaining the context data comprising location data.

13. The method according to claim 12, wherein generating, based on the adjusted first notification setting parameter, one or more notifications comprises generating the one or more notifications based on the adjusted first notification setting parameter and location data.

14. The method according to claim 6, wherein displaying the one or more notifications including the first notification comprises displaying the first notification on a locked screen.

15. The method according to claim 6, wherein displaying the one or more notifications including the first notification comprises displaying the first notification on an unlocked screen.

16. The method according to claim 6, wherein when the accessory device is in a locked state, the method comprising:
detecting an authentication input to unlock the device;
in response to detecting the authentication input to unlock the device, verifying the authentication input;
unlocking the accessory device in accordance with successful verification of the authentication input; and,
in response to unlocking of the accessory device, in accordance with successful verification of the authentication input, displaying a first user interface including the first notification.

17. The method according to claim 5, the method comprising:
detecting a biometric input,
in response to detecting the biometric input, verifying the biometric input;
in accordance with successful verification of the biometric input, displaying the one or more notifications including the first notification comprises displaying a long version of the first notification;
in accordance with unsuccessful verification of the biometric input, displaying the one or more notifications including the first notification comprises displaying a short version of the first notification.

18. The method according to claim 5, wherein displaying the one or more notifications including the first notification comprises displaying, on the display, the first notification indicative of one or more operating states.

19. The method according to claim 5, the method comprising:
detecting a second input selecting the first notification;
in response to detecting the second input, opening the medical user application.

20. The method according to claim 19, the method comprising:
in response to opening the medical system user application, displaying a second user interface comprising a third user interface object representing the current operating state of the medical appliance and a fourth user interface object representing the one or more future operating states of the medical appliance.

21. The method according to claim 1, wherein the notification parameters comprise a frequency of notification, a time to notify, a recurrence, and/or a time to change medical appliance.

22. An accessory device, wherein the accessory device forms part of a medical system, the accessory device comprising:
a memory;
a processor operatively connected to the interface and to the memory; and
an interface configured to communicate with one or more devices of the medical system, the one or more devices comprising a medical appliance configured to be placed on a skin surface of a user; wherein the medical appliance comprises a base plate;
wherein the interface comprises a display;
wherein the accessory device is configured to perform any of the methods according to claim 1.

* * * * *

UNITED STATES PATENT AND TRADEMARK OFFICE
CERTIFICATE OF CORRECTION

PATENT NO. : 11,903,728 B2
APPLICATION NO. : 16/979531
DATED : February 20, 2024
INVENTOR(S) : Svanegaard et al.

It is certified that error appears in the above-identified patent and that said Letters Patent is hereby corrected as shown below:

In the Claims

At Column 54, in Claim 1 at Line 17, "of medical system user application," should read: "of a medial system user application,"

At Column 56, in Claim 19 at Line 22, "opening the medical user application." should read: "opening the medical system user application."

Signed and Sealed this
Eighteenth Day of June, 2024

Katherine Kelly Vidal
*Director of the United States Patent and Trademark Office*